(12) United States Patent
Chen et al.

(10) Patent No.: US 12,410,463 B2
(45) Date of Patent: Sep. 9, 2025

(54) MOLECULAR BEACONS

(75) Inventors: Antony Kuang-Shih Chen, Rockville, MD (US); Andrew Tsourkas, Philadelphia, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

(21) Appl. No.: 13/496,546

(22) PCT Filed: Sep. 17, 2010

(86) PCT No.: PCT/US2010/049301
§ 371 (c)(1),
(2), (4) Date: May 29, 2012

(87) PCT Pub. No.: WO2011/035135
PCT Pub. Date: Mar. 24, 2011

(65) Prior Publication Data
US 2012/0237451 A1 Sep. 20, 2012

Related U.S. Application Data

(60) Provisional application No. 61/243,586, filed on Sep. 18, 2009.

(51) Int. Cl.
*C12Q 1/6876* (2018.01)
*C12Q 1/6818* (2018.01)

(52) U.S. Cl.
CPC .................. *C12Q 1/6818* (2013.01)

(58) Field of Classification Search
CPC ............ C12Q 1/6818; C12Q 1/6876
See application file for complete search history.

(56) References Cited

U.S. PATENT DOCUMENTS

| | | | |
|---|---|---|---|
| 5,866,336 A | 2/1999 | Nazarenko et al. | |
| 5,925,517 A | 7/1999 | Tyagi et al. | |
| 6,028,290 A | 2/2000 | Yasuhara et al. | |
| 6,060,240 A | 5/2000 | Kamb et al. | |
| 6,103,476 A | 8/2000 | Tyagi et al. | |
| 6,150,107 A | 11/2000 | Glazer et al. | |
| 6,297,016 B1 | 10/2001 | Egholm et al. | |
| 6,316,230 B1 | 11/2001 | Egholm et al. | |
| 6,316,610 B2 | 11/2001 | Lee et al. | |
| 2003/0129611 A1 | 7/2003 | Bao et al. | |
| 2004/0110214 A1* | 6/2004 | Kim et al. | |
| 2005/0042618 A1 | 2/2005 | Heindl et al. | |
| 2005/0053942 A1* | 3/2005 | Kauppinen | C12Q 1/6806 435/6.12 |
| 2005/0130167 A1 | 6/2005 | Bao et al. | |
| 2005/0202433 A1* | 9/2005 | Van Beuningen | C12Q 1/6823 435/287.2 |
| 2005/0287548 A1 | 12/2005 | Bao et al. | |
| 2006/0127940 A1 | 6/2006 | Bao et al. | |
| 2006/0246500 A1 | 11/2006 | Browne | |
| 2007/0020664 A1* | 1/2007 | Gupta | C12Q 1/6883 435/6.12 |
| 2007/0269825 A1* | 11/2007 | Wang | C12Q 1/6858 435/5 |
| 2008/0299549 A1* | 12/2008 | Sorge | C12Q 1/6844 435/6.1 |
| 2009/0098612 A1* | 4/2009 | Rhee | C12Q 1/6855 435/91.2 |
| 2009/0104614 A1 | 4/2009 | Tsourkas et al. | |
| 2009/0117540 A1* | 5/2009 | Sorge | G01N 33/5308 435/200 |
| 2009/0156416 A1 | 6/2009 | Tan et al. | |
| 2010/0196887 A1 | 8/2010 | Hyldig-Nielsen et al. | |

FOREIGN PATENT DOCUMENTS

WO   WO 07/106900   9/2007

OTHER PUBLICATIONS

Chen et al., Ratiometric bimolecular beacons for the sensitive detection of RNA in single living cells, Nucleic Acids Research, 2010, vol. 38, No. 14, e148.*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"Viruses" (Wikipedia.com, accessed Nov. 24, 2012).*
"How many species of bacteria are there" (wisegeek.com; accessed Sep. 23, 2011).*
"List of sequenced bacterial genomes" (Wikipedia.com; accessed Jan. 24, 2014).*
"Viruses", Wikipedia.com, accessed Nov. 24, 2012. (Year: 2012).*
"How many species of bacteria are there", wisegeek.com; accessed Sep. 23, 2011. (Year: 2011).*
Sharon Begley, "Psst, the human genome was never completely sequenced", STATNews, Jun. 20, 2017. (Year: 2017).*
Forster et al., "A human gut bacterial genome and culture collection for improved metagenomics analyses", Nature Biotechnology, vol. 37, Feb. 2019, pp. 186-192. (Year: 2019).*
"List of sequenced bacterial genomes", Wikipedia.com; accessed Jan. 24, 2014. (Year: 2014).*
Santangelo et al. Dual FRET molecular beacons for mRNA detection in living cells. Nucleic Acids Research, vol. 32, No. 6, e57 p. 1-9. esp: abstract, p. 1 section entitled "Molecular beacon design and synthesis", p. 3 section entitled "Dual FRET Molecular" Fig. 1, (2004).
Gidwani et al. "Hybridization kinetics of double-stranded DNA probes for rapid molecular analysis" vol. 134, No. 8, pp. 1675-1681, Aug. 2009.

(Continued)

*Primary Examiner* — Bradley L. Sisson
(74) *Attorney, Agent, or Firm* — Mark S. Cohen; PEARL COHEN ZEDEK LATZER BARATZ LLP

(57) ABSTRACT

The invention provides novel compositions and methods for the detection of a target molecule. Specifically, the invention provides a bimolecular beacon composition comprising two nucleic acid molecules, and methods thereof. One of the nucleic acid molecule is operably linked to a reporter detectable label and the other nucleic acid molecule is operably linked to a reference detectable label and a quencher. In some embodiments, at least one of the nucleic acid molecules comprises a single stranded overhang.

10 Claims, 6 Drawing Sheets

Specification includes a Sequence Listing.

(56) References Cited

OTHER PUBLICATIONS

Chen et al. "Avoiding false-positive signals with nucleasevulnerable molecular beacons in single living cells" Nucleic Acids Research, vol. 35, No. 16 e105 p. 1-12. (2007).

Bao et al. Engineering Nanostructured Probes for Sensitive Intracellular Gene Detection. Mech Chem Biosyst, vol. 1, No. 1, pp. 23-36, Mar. 2004.

Zeng et al. "Structural requirements for pre-microRNA binding and nuclear export by Exportin 5" Nucleic Acids Research, vol. 32, No. 16, pp. 4776-4785, Sep. 8, 2004.

Tyagi et al. "Molecular Beacons: Probes that Fluoresce upon Hybridization" Nature Biotechnology, vol. 14, No. 3, pp. 303-308, Mar. 1996.

Kirk et al. "Single nucleotide polymorphism seeking long term association with complex disease" Nucleic Acids Res. 1, vol. 30, No. 15, pp. 3295-3311, Aug. 2002.

Bao et al. "Fluorescent Probes for Live-Cell RNA Detection" Annu. Rev. Biomed. Eng. Vol 11, pp. 25-47, (2009).

Bengra et al. Genotyping of Essential Hypertension Single-Nucleotide Polymorphisms by a Homogeneous PCR Method with Universal Energy Transfer Primers. Clinical Chemistry, vol. 48, No. 12, pp. 2131-2140, Dec. 2002.

Bratu et al. "Visualizing the distribution and transport of mRNAs in living cells" PNAS, vol. 100, No. 23, pp. 13308-13313, Nov. 11, 2003.

Chen et al., Ratiometric bimolecular beacons for the sensitive detection of RNA in single living cells. Nucleic Acids Research, vol. 38, No. 14, e148, Aug. 2010.

Chen et al. "Efficient cytosolic delivery of molecular beacon conjugates and flow cytometric analysis of target RNA" Nucleic Acids Research , vol. 36, No. 12, e69, Jul. 2008.

Tsourkas et al. "Hybridization of 2'-0-methyl and 2'-deoxy molecular beacons to RNA and DNA targets" Nucleic Acids Research, vol. 30, No. 23,5168-5174, (2002).

Ohrt et al. "In situ fluorescence analysis demonstrates active siRNA exclusion from the nucleus by Exportin 5" Nucleic Acids Research, vol. 34, No. 5, pp. 1369-1380, (2006).

Tyagi et al "Multicolor molecular beacons for allele discrimination" Nat Biotechnol. 16(1):49-53, Jan. 1998.

Ju et al. "Fluorescence energy transfer dye-labeled primers for DNA sequencing and analysis" Proc. Natl. Acad. Sci. USA 92:4347 4351, 1995.

Stein et al. "Physicochemical Properties of Phosphorothioate Oligodeoxynucleotides" Nucleic Acids Research 16:3209 3221, (1988).

Sarin et al., "Inhibition of acquired immunodeficiency syndrome virus by oligodeoxynucleoside methylphosphonates", 1988, Proc. Natl. Acad. Sci. U.S.A. 85:7448 7451.

Vet et al., "Design and Optimization of Molecular Beacon Real-Time Polymerase Chain Reaction Assays", Methods in Molecular Biology, vol. 288: Oligonucleotide Synthesis: Methods and Applications, pp. 273-290.

Marras et al., "Genotyping Single Nucleotide Polymorphisms with Molecular Beacons", Kwok, P.Y. (ed.), Single Nucleotide Polymorphisms: methods and protocols. The Humana Press Inc., vol. 212, pp. 111-128.

\* cited by examiner

MOLECULAR BEACONS

CROSS-REFERENCE TO RELATED APPLICATIONS

This application is a National Phase Application of PCT International Application No. PCT/US10/49301, International Filing Date Sep. 17, 2010, claiming priority to U.S. Provisional Patent Applications 61/243,586 and 61/244,378, filed Sep. 18, 2010 and Sep. 21, 2009, respectively, all of which are incorporated by reference herein in their entirety.

GOVERNMENT INTEREST STATEMENT

This invention was made with government support under grant number CA116102 awarded by the National Institute of Health. The government has certain rights in the invention.

FIELD OF THE INVENTION

The invention relates to novel compositions and methods for detecting a target molecule. Specifically, the invention relates to a bimolecular beacon composition comprising two oligo nucleic acid molecules, and methods thereof.

BACKGROUND OF THE INVENTION

Among the technologies currently under development for living cell gene detection and quantification, the most promising one is probably molecular beacons. Conventional molecular beacons are single-stranded oligonucleotide hybridisation probes that form a stem-and-loop structure. The loop portion contains the sequence complementary to the target nucleic acid (either DNA or RNA). The stem is formed due to hydridisation of the complementary sequence of the 3'end with the 5'end. The stem can be unrelated to the target and is double-stranded. One arm of the stem is labeled with a fluorescent dye (fluorophore), whereas the other one is coupled to a quenching molecule. In the stem-loop state the probe does not produce fluorescence because the energy of the fluorophore is transferred to the quenching molecule. When the molecular beacon hybridises to the target, the stem-loop structure is lost and the quencher and fluorophore are separated. At that stage, the fluorescence emitted by the fluorophore can be detected and quantified.

One of the problems with conventional molecular beacons is that when they are introduced into living cells, they are rapidly sequestered into the nucleus and once there, they elicit a bright false-positive signal. The presence of false-positive signals in the nucleus has significant implications when trying to use MBs to measure gene expression. For example, non-specific opening of MBs can easily be confused with MB hybridization and lead to ambiguous results. Further, non-specific opening results in a significant loss in the sensitivity and dynamic range of MBs in living cells.

Another problem with the conventional molecular beacons is that they are not capable of providing accurate information on cell-to-cell variations in gene expression. This deficiency stems from the inability to accurately account for the large variations in cellular fluorescence that results from heterogeneous delivery. For example, cells that have no or low amounts of internalized MBs could easily be mistaken for cells with low gene expression, thus resulting in a false-negative. Conversely, cells that have high levels of internalized MBs generally exhibit a measurable background that can easily be mistaken for probe hybridization, i.e. false-positive. The inability to measure the efficiency of MB delivery with current MB designs limits their use to studying highly expressed RNA, i.e. studies where fluorescence enhancement upon MB hybridization is significantly greater than the cell-to-cell variability in fluorescence that results from heterogeneous delivery.

Yet another problem with the conventional molecular beacons is that they are rapidly sequestered into the nucleus upon introduction into living cells and they suffer from the inability to be exported from the nucleus.

Accordingly, there exists a need for an improved molecular beacons for detecting a target molecule in cells and tissues.

SUMMARY OF THE INVENTION

In one embodiment, the invention provides a bimolecular beacon comprising: a first nucleic acid operably linked to a first detectable label at one of its ends and a second nucleic acid operably linked to a second detectable label at its one end and a quencher at its other end.

In another embodiment, the invention provides a composition comprising: a first nucleic acid operably linked to a first detectable label at one of its ends and a second nucleic acid operably linked to a second detectable label at its one end and a quencher at its other end.

In another embodiment, the invention provides an oligonucleotide probe comprising: a first nucleic acid operably linked to a first detectable label at one of its ends and a second nucleic acid operably linked to a second detectable label at its one end and a quencher at its other end.

In another embodiment, the invention provides a kit comprising: a first nucleic acid operably linked to a first detectable label at one of its ends and a second nucleic acid operably linked to a second detectable label at its one end and a quencher at its other end.

In another embodiment, the invention provides a method for detecting a polymorphism associated with target gene comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a relative fluorescent intensity of said first and second detectable labels, whereby the relative intensities indicate the presence or absence of said polymorphism, thereby detecting said polymorphism.

In another embodiment, the invention provides a method for detecting the expression level of a target gene comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a relative fluorescent intensity of said first and second detectable labels, whereby the relative intensities indicate the expression level of said target gene, thereby detecting the expression level of said target gene.

In another embodiment, the invention provides a method for diagnosis of a disease in a subject comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a relative fluorescent intensity of said first and second detectable labels, whereby the relative intensities indicate the presence or absence of said disease in said subject, thereby diagnosing said disease.

In another embodiment, the invention provides a method for monitoring a transfection efficiency comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a fluorescent intensity of said first and second detectable labels, whereby the relative intensities indicate said transfection efficiency.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1A:
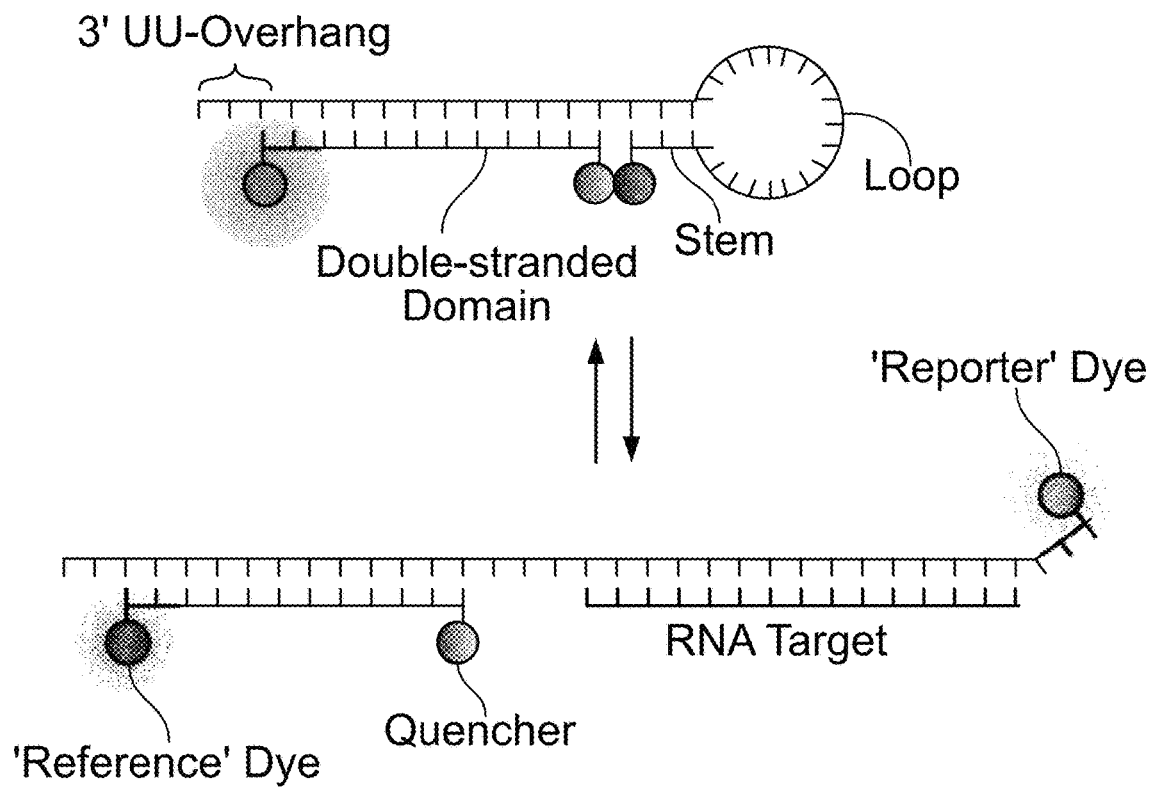
FIG. 1. Schematic and fluorescent emission spectra of Ratiometric BiMolecular Beacons (RBMBs). (A) RBMBs are hairpin-forming oligonucleotide probes that are labeled with a reporter fluorophore, reference fluorophore, and quencher. In the absence of complementary targets the reporter fluorophore and quencher are held in close proximity resulting a low fluorescence state. In the presence of target, the reporter fluorophore and quencher are separated and fluorescence is restored. The reference fluorophore remains unquenched regardless of the RBMB conformation. The long double-stranded domain with a UU-overhang was designed to mimic the structure of siRNA and is used to drive nuclear export. (B) Emission spectra of an RBMB (Cy5 reporter, Iowa Black RQ quencher, and an IRdye® 800 reference dye) in the absence (○) and presence (♦) of excess complementary RNA targets.

The invention relates to novel compositions and methods for detecting a target molecule. Specifically, the invention relates to a bimolecular beacon composition comprising two nucleic acid molecules, and methods thereof.

In one embodiment, provided herein is a bimolecular beacon comprising: a first nucleic acid operably linked to a first detectable label at one of its ends and a second nucleic acid operably linked to a second detectable label at its one end and a quencher at its other end. In another embodiment, provided herein is a composition comprising: a first nucleic acid operably linked to a first detectable label at one of its ends and a second nucleic acid operably linked to a second detectable label at its one end and a quencher at its other end.

In another embodiment, provided herein is an oligonucleotide probe comprising: a first nucleic acid operably linked to a first detectable label at one of its ends and a second nucleic acid operably linked to a second detectable label at its one end and a quencher at its other end. In another embodiment, provided herein is a kit comprising: a first nucleic acid operably linked to a first detectable label at one of its ends and a second nucleic acid operably linked to a second detectable label at its one end and a quencher at its other end.

In another embodiment, provided herein is a method for detecting a polymorphism associated with target gene comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a relative fluorescent intensity of said first and second detectable labels, whereby the relative intensities indicate the presence or absence of said polymorphism, thereby detecting said polymorphism. In another embodiment, provided herein is a method for detecting the expression level of a target gene comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a relative fluorescent intensity of said first and second detectable labels, whereby the relative intensities indicate the expression level of said target gene, thereby detecting the expression level of said target gene.

In another embodiment, provided herein is a method for diagnosis of a disease in a subject comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a relative fluorescent intensity of said first and second detectable labels, whereby the relative intensities indicate the presence of said disease in said subject, thereby diagnosing said disease.

In another embodiment, provided herein is a method for monitoring a transfection efficiency comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a relative fluorescent intensity of said first and second detectable labels, whereby the relative intensities indicate said transfection efficiency.

The biomolecular beacon of the invention is capable of emitting both reporter and reference fluorescence with the same probe, and thereby accounting for cell-to-cell variability and allowing confident analysis of gene expression in individual cells. The biomolecular beacon of the invention allows simpler and more flexible transfection procedures, allows monitoring of gene expression in large numbers of cells, and makes ratiometric measurements reliable during short and long term expression studies. Furthermore, the biomolecular beacon of the invention enhances the ability of the beacon to be exported from the nucleus.

The bimolecular beacon comprises at least two oligo nucleic acid molecules. The first nucleic acid molecule is longer than the second nucleic acid molecule. In one embodiment, a portion of the first nucleic acid is complementary to a portion of the second nucleic acid to form a double-stranded stem hybrid. In another embodiment, the first nucleic acid is complementary to a nucleic acid sequence of said target gene. In an exemplary embodiment, this portion complementary to the target gene forms a loop when the first nucleic acid is hybridized with the second nucleic acid.

In another embodiment, the first nucleic acid comprises an overhang at its 3' end and a detectable label at its 5' end. The overhang can comprise single stand sequence having at least two base pairs. In a particular embodiment, the overhang comprises the single strand sequence UU. The overhang facilitates various functions including the nuclear export of the molecular beacon.

In one embodiment, the quencher is operably linked to 3' end of the second nucleic acid molecule. In another embodiment, the quencher is operably linked to 5' end of the first nucleic acid molecule.

In another embodiment, the first nucleic acid comprises a first detectable label (e.g., a reporter label) at its 5' end. In another embodiment, the second nucleic acid comprises a second detectable label (e.g., a reference detectable label) at its 5' end. The quencher may interact with the first detectable label and does not interact with said second detectable label. In some embodiments, the quencher quenches the activity of the first detectable label when both first and second nucleic acids are hybridized to each other to form a stem hybrid.

In another embodiment, the second detectable label (e.g., a reference detectable label) emits its signal when both first and second nucleic acids are hybridized to each other to form a stem hybrid. In one embodiment, both the first and second detectable labels (e.g., both reference and reporter detectable labels) emit their respective signal when the loop portion of the first nucleic acid is hybridized to a sequence of a target gene.

The first or second detectable label may emit a resonance energy transfer signal. The resonance energy transfer signal can be due to a fluorescence resonance energy transfer (FRET), a luminescence resonance energy transfer (LRET), or others known to one of skilled in the art.

The detectable labels can be linked to either 5' or 3' ends of the nucleic acids by any suitable method known to one of skilled in the art. In some embodiments, the detectable label is conjugated to 5' or 3' ends of the nucleic acids via covalent bonding or affinity bonding.

The term "detectable label" refers in one embodiment to a composition or moiety that is detectable by spectroscopic, photochemical, biochemical, immunochemical, electromagnetic, radiochemical (e.g., using technetium-$^{99}$m ($^{99}$mTc)), or chemical means such as fluorescence, chemifluorescence, or chemiluminescence, or any other appropriate means. Methods and compositions for detectably labeling molecules, such as oligonucleotides, PNA-DNA hybrids, etc. are well known in the art. See, e.g., U.S. Pat. Nos. 6,316,230; 6,297,016; 6,316,610; 6,060,240; 6,150,107; and 6,028,290, each of which are hereby incorporated by reference in their entirety.

In one embodiment, the detectable label is a photoluminescent dye. Examples of the photoluminescent dye used in the beacons, methods and kits of the invention include, but are not limited to, fluorescein, phycoerythrin, CY3, CY5, allophycocyanine, Texas Red, peridenin chlorophyll, cyanine, FAM, JOE, TAMRA, TET, VIC, or a combination thereof. In another embodiment, the FAM is 6-carboxyfluorescein (6-FAM).

In another embodiment, the detectable label is any organic dye. In another embodiment, the detectable label is a phycobiliprotein, for example, but are not limited to, Red Phycoerythrin (RPE), Blue Phycoerythrin (BPE), and Allophycocyanin (APC). In another embodiment, the detectable label is a lanthanide and/or chelator molecule, for example, but are not limited to, DTPA-cytosine, DTPA-cs124, BCPDA, BHHCT, or Isocyanato-EDTA.

In one embodiment, molecular beacon probes according to the present invention utilize any photoluminescent moiety as a detectable moiety. Typically these are dyes. In another embodiment these are fluorescent dyes. Photoluminescence is any process in which a material is excited by radiation such as light in one embodiment, is raised to an excited electronic or vibronic state, and subsequently re-emits that excitation energy as a photon of light. Such processes include in one embodiment fluorescence, which denotes emission accompanying descent from an excited state with paired electrons (a "singlet" state) or unpaired electrons (a "triplet" state) to a lower state with the same multiplicity, i.e., a quantum-mechanically "allowed" transition. Photoluminescence includes in another embodiment phosphorescence which denotes emission accompanying descent from an excited triplet or singlet state to a lower state of different multiplicity, i.e., a quantum mechanically "forbidden" transition. Compared to "allowed" transitions, "forbidden" transitions are associated with relatively longer excited state lifetimes.

Suitable fluorophores for use in the molecular beacons, kits and methods of the invention include, but are not limited to, 6-carboxyfluorescein (6FAM), tetrachloro-6-carboxyfluorescein (TET), or 2'-chloro-7'-phenyl-1,4-dichloro-6-carboxyfluorescein (VIC). Other examples of fluorophores include, but are not limited to, 4-acetamido-4'-isothiocyanatostilbene-2,2' disulfonic acid acridine and derivatives: acridine acridine isothiocyanate 5-(2'-aminoethyl)aminonaphthalene-1-sulfonic acid (EDANS) 4-amino-N-[3-vinylsulfonyl)phenyl]naphthalimide-3,5disulfonate (LuciferYel-low VS) N-(4-anilino-1-naphthyl)maleimide Anthranilamide Brilliant Yellow coumarin and derivatives: coumarin 7-amino-4-methylcoumarin (AMC, Coumarin 120) 7-amino-4-trifluoromethylcoumarin (Coumarin 151) cyanosine 4'-6-diaminidino-2-phenylindole (DAPI) 5',5"-dibromopyrogallol-sulfonephthalein (Bromopyrogallol Red) 7-diethylamino-3-(4'-isothiocyanatophenyl)-4-methylcoumarin diethylenetriamine pentaacetate 4-(4'-diisothiocyanatodihydro-stilbene-2,2'-disulfonic acid 4,4'-diisothiocyanatostilbene-2,2'-disulfonic acid 5-[dimethylamino] naphthalene-1-sulfonyl chloride (DNS, dansyl chloride) 4-(4'-dimethylaminophenylazo)benzoic acid (DABCYL) 4-dimethylaminophenylazophenyl-4'-isothiocyanate (DABITC) eosin and derivatives: eosin eosin isothiocyanate erythrosin and derivatives: erythrosin B erythrosin isothiocyanate ethidium fluorescein and derivatives: 5-carboxyfluorescein (FAM) 5-(4,6-dichlorotriazin-2-yl)aminofluorescein (DTAF) 2'7'-dimethoxy-4'5'-dichloro-6-carboxyfluorescein (JOE) fluorescein fluorescein isothiocyanate QFITC (XRITC) fluorescamine IR144 IR1446 Malachite Green isothiocyanate 4-methylumbelliferone ortho cresolphthalein nitrotyrosine pararosaniline Phenol Red B-phycoerythrin o-phthaldialdehyde pyrene and derivatives: pyrene pyrene butyrate succinimidyl 1-pyrene butyrate Reactive Red 4 (Cibacron® Brilliant Red 3B-A) rhodamine and derivatives: 6-carboxy-X-rhodamine (ROX) 6-carboxyrhodamine (R6G) lissamine rhodamine B sulfonyl chloride rhodamine (Rhod) rhodamine B rhodamine 123 rhodamine X isothiocyanate sulforhodamine B sulforhodamine 101 sulfonyl chloride derivative of sulforhodamine 101 (Texas Red) N,N,N',N'-tetramethyl-6-carboxyrhodamine (TAMRA) tetramethyl rhodamine tetramethyl rhodamine isothiocyanate (TRITC) riboflavin rosolic acid terbium chelate derivatives.

In one embodiment, the molecular beacon of the invention, which is used in the methods and kits of the invention, comprises a quencher disposed on the opposing end of, for example, the second detectable label. In another embodiment, "quencher" as used herein means a molecule that, in close proximity to a fluorophore, takes up emission energy generated by the donor and either dissipates the energy as heat or emits light of a longer wavelength than the emission wavelength of the donor. The quenching can act in another embodiment, via proximal (i.e. collisional) quenching or by Forster or fluorescence resonance energy transfer ("FRET") in other embodiments. Quenching by FRET is used in one embodiment when TAQMAN probes are used while in another embodiment, proximal quenching is used in molecular beacon and scorpion type probes. In another embodiment, the resonance energy signals are due to luminescence resonance energy transfer (LRET). The quencher moiety may be a dye such as TAMRA or may be a non-fluorescent molecule such as 4-(4-dimethylaminophenylazo)benzoic acid (DABCYL). See Tyagi et al., Nature Biotechnology 16:49-53 (1998). When irradiated, the excited fluorescent donor transfers energy to the nearby quenching moiety rather than fluorescing. Thus, the close proximity of the donor and quencher prevents emission of donor fluorescence while the probe is intact.

Suitable quenchers include, but are not limited to, tetramethylcarboxyrhodamine (TAMRA) 4-(4-dimethylaminophenylazo)benzoic acid ("DABCYL" or a DABCYL analog) and the like.

In some embodiments, probes are preferably modified during synthesis, such that a modified T-base is introduced into a designated position by the use of Amino-Modifier C6 dT (Glen Research), and a primary amino group is incorporated on the modified T-base, as described by Ju et al. (1995, Proc. Natl. Acad. Sci. USA 92:4347 4351). These modifications may be used for subsequent incorporation of fluorescent dyes into designated positions of the first or second nucleic acids of the present invention.

In yet another embodiment, the first or second nucleic acids of the invention may be further labeled with any other art-known detectable marker, including radioactive labels such as $^{32}P$, $^{35}S$, $^{3}H$, and the like, or with enzymatic markers that produce detectable signals when a particular chemical reaction is conducted, such as alkaline phosphatase or horseradish peroxidase. Such enzymatic markers are preferably heat stable, so as to survive the denaturing steps of the amplification process. The first or second nucleic acids may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. The first or second nucleic acids may be supplementally labeled during chemical synthesis or the supplemental label may be attached after synthesis by methods known in the art.

In one embodiment, the invention provides a bimolecular beacon having the first nucleic acid that comprises a stem and a loop structure, wherein said loop has a sequence complementary to a coding, or non coding region of target gene. In another embodiment, "complementary" indicates that the oligonucleotide has a base sequence containing an at least 10 contiguous base region that is at least 70% complementary, or in another embodiment at least 80% complementary, or in another embodiment at least 90% complementary, or in another embodiment 100% complementary to an-at least 10 contiguous base region present in a target gene sequence. Those skilled in the art will readily appreciate modifications that could be made to the hybridization assay conditions at various percentages of complementarity to permit hybridization of the oligonucleotide to the target sequence while preventing unacceptable levels of non-specific hybridization. The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-3 base mismatches.

In one embodiment, the invention provides a bimolecular beacon having the first nucleic acid that comprises a stem and a loop structure, wherein said loop has a sequence complementary to a coding region of a target gene. The term "coding region" refers in one embodiment to a sequence of a nucleic acid or its complement, or a part thereof, that can be transcribed and/or translated to produce the mRNA for and/or the polypeptide or a fragment thereof. In another embodiment, coding sequences include exons in a genomic DNA or immature primary RNA transcripts, which are joined together in one embodiment, by the cell's biochemical processes, providing a mature mRNA. The anti-sense strand is the complement of such a nucleic acid, and the skilled artisan would readily recognize that the encoding sequence can be deduced therefrom.

In another embodiment, the invention provides a bimolecular beacon having the first nucleic acid that comprises a stem and a loop structure, wherein said loop has a sequence complementary to a non-coding region of a target gene. In one embodiment, the term "non-coding region" refers to a sequence of a nucleic acid or its complement, or a part thereof, that is not transcribed into amino acid in vivo, or where tRNA does not interact to place or attempt to place an amino acid in another embodiment. Non-coding sequences include in one embodiment both intron sequences in genomic DNA or immature primary RNA transcripts, and gene-associated sequences such as promoters, enhancers, silencers, etc., in other embodiments.

In another embodiment, the invention provides a bimolecular beacon having the first nucleic acid that comprises a stem and a loop structure, wherein said loop has a sequence complementary to region for detecting polymorphism of a target gene.

In another embodiment, the invention provides a bimolecular beacon having the first nucleic acid that comprises a stem and a loop structure, wherein said loop has a sequence complementary to a short non-coding RNA. Short non-coding RNAs include miRNAs, piRNAs, snoRNAs, siRNAs, etc.

The bimolecular beacon having the first and second nucleic acids, wherein the first nucleic acid is longer than the second nucleic acid. In certain embodiments, the invention provides that the first or second nucleic acid comprises from 5 to 100 nucleotides, 10 to 50 nucleotides, or 15, 16, 17, 18, 19, 20, 21, 22, 23, 24, 25, 26, 27, 28, 29 or 30 nucleotides. In other preferred embodiments, the nucleic acids comprise a 2'-O-methyl nucleotide backbone, among many alternative or synthetic nucleotides, described below.

The term "stem," as used herein, refers to a double-helical region formed by base pairing between adjacent, inverted, complementary sequences in a single strand of RNA or DNA. The term "loop" refers to a loop of unpaired bases. The term "stem-loop" structure refers to a hairpin structure comprising at least one stem and further comprising a loop of unpaired bases. In one embodiment, the first nucleic acid alone is capable of forming a stem-loop structure. In one embodiment, the stem portion in the first nucleic acid comprises from 0 to 20 nucleotides. In another embodiment, the stem hybrid is formed by the pairing or annealing of complementary arm sequences of a portion of the first nucleic acid and the second nucleic acid. In another embodiment, the stem hybrid between the first and second nucleic acid sequences comprises a double stranded domain. In another embodiment, the stem hybrid between the first and second nucleic acid sequences comprises from 5 to 100 nucleotides. In another embodiment, the loop in the first nucleic acid sequence comprises from 3 to 50 nucleotides. In another embodiment, the overhang portion in the first nucleic acid sequence comprises from 0 to 50 nucleotides.

One aspect of the invention pertains to nucleic acids sufficient for use as hybridization probes for the identification of a target nucleic acid (e.g., DNA or mRNA). As used herein, the term "nucleic acid" is intended to include DNA molecules (e.g., cDNA or genomic DNA) and RNA molecules (e.g., mRNA) and analogs of the DNA or RNA generated using nucleotide analogs. As referred to herein, nucleic acids that are "complementary" can be perfectly or imperfectly complementary, as long as the desired property resulting from the complementarity is not lost, e.g., ability to hybridize.

The nucleic acids of the present invention may be substantially isolated or alternatively unpurified. An "isolated" or "purified" nucleic acid is one that is substantially separated from other nucleic acid molecules that are present in the natural source of the nucleic acid. Preferably, an "isolated" nucleic acid is substantially free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule can be substantially free of other cellular material, or culture medium when produced by recombinant techniques, or chemical precursors or other chemicals when chemically synthesized. (See Sambrook et al. 1989, Molecular Cloning: A Laboratory Manual. 2nd, ed., Cold Spring Harbor Laboratory, Cold Spring Harbor Laboratory Press, Cold Spring Harbor, N.Y.).

The bimolecular beacon typically comprises substantially purified first and second nucleic acids. The first nucleic acid of the beacon typically comprises a region of nucleotide sequence that hybridizes to at least about 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 consecutive nucleotides of a target nucleic acid. The target nucleic acid can be a sense strand of one of the target nucleic acid sequences, an anti-sense sequence, or naturally occurring mutants thereof. Preferably, the nucleic acid target is an RNA.

The bimolecular beacon of the invention can be used as a part of a genomic marker test kit for identifying cells which express a particular protein, such as by measuring a level of the protein-encoding nucleic acid in a sample of cells, e.g., detecting the target nucleic acid mRNA levels or determining whether the gene encoding the mRNA has been mutated or deleted.

In an additional embodiment, the first nucleic acid molecule of the invention comprises a nucleic acid probe sequence that hybridizes, e.g., hybridizes under stringent conditions, to a target nucleotide sequence of interest. These hybridization conditions include washing with a solution having a salt concentration of about 0.02 molar at pH 7 at about 60° C. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, John Wiley & Sons, N.Y. (1989) 6.3.1 6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. As used herein, a "naturally-occurring" nucleic acid molecule refers to an RNA or DNA molecule having a nucleotide sequence that occurs in nature (e.g., encodes a natural protein).

The beacon nucleic acids of the invention can be DNA or RNA or chimeric mixtures or derivatives or modified versions thereof, so long as it is still capable of hybridizing to the desired target nucleic acid. In addition to being labeled with a detection label, the nucleic acid sequence can be modified at the base moiety, sugar moiety, or phosphate backbone, and may include other appending groups or labels.

In one embodiment, the first or second nucleic acid of the invention can be chemically synthesized using naturally occurring nucleotides or variously modified nucleotides designed to increase the biological stability of the molecules or to increase the physical stability of the duplex formed between the complimentary nucleic acids, e.g., phosphorothioate derivatives and acridine substituted nucleotides can be used. A preferred example of a class of modified nucleotides which can be used to generate the nucleic acid probes is a 2'-O-methyl nucleotide. Additional examples of modified nucleotides which can be used to generate the nucleic acid probes include for example 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

In another embodiment, the first or second nucleic acid of the invention comprises at least one modified sugar moiety selected from the group including but not limited to arabinose, 2-fluoroarabinose, xylulose, and hexose. In yet another embodiment, the first or second nucleic acid of the present invention comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof. As stated above, a preferred example of a modified nucleotide which can be used to generate the nucleic acid probes is a 2'-O-methyl nucleotide.

Nucleic acids of the invention can be synthesized by standard methods known in the art, e.g. by use of an automated DNA synthesizer (such as are commercially available from Biosearch, Applied Biosystems, etc.). For examples, phosphorothioate oligonucleotides can be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448 7451), etc.

Once the desired oligonucleotide is synthesized, it is cleaved from the solid support on which it was synthesized and treated, by methods known in the art, to remove any protecting groups present. The oligonucleotide may then be purified by any method known in the art, including, for example, extraction and gel purification. The concentration and purity of the oligonucleotide can be determined by examining oligonucleotide that has been separated on an acrylamide gel, or by measuring the optical density at 260 in a spectrophotometer.

In one embodiment, the sensitivity of cellular imaging and quantification of gene expression using molecular beacons is severely limited by the degradation of oligonucleotide backbone by nucleases. To overcome this difficulty, in another embodiment, molecular beacons are synthesized with nuclease-resistant backbone chemistries, such as phosphorothioate in one embodiment, or peptide nucleic acid (PNA) and 2'-O-methyl modifications in other embodiments. In some embodiments, the nuclease resistant chemistry used in the beacons, methods and kits of the invention comprises phosphorothioate-modified backbone.

In one embodiment, beacons modified with sugar modified-'North' (3'-endo-2'-exo) conformationally constrained nucleosides, or base-constraining oxetane (OXE) modifications (oxetane, 1-(1',3'-O-anhydro-.beta.-D-psicofuranosyl nucleosides), are used to protect the beacon from nuclease activity by modifying the beacon's backbone. The modifications, in another embodiment makes the beacon so modified be delivered to the cells with greater efficiency, making resolution of the methods and kits of the invention higher and detection more accurate.

In one embodiment, the effective concentration of the molecular beacon used in the methods and kits of the invention is between about 1 and 100 nM. In another embodiment, the effective concentration of the molecular beacon is between about 100 nM and 1 µM, or in another embodiment between about 1 and 5 µM, or in another embodiment between about 5 and 10 µM, or in another embodiment between about 10 and 20 µM, or in another embodiment between about 20 and 25 µM, or in another embodiment between about 25 and 30 µM, or in another embodiment between about 30 and 35 µM, or in another embodiment between about 35 and 40 µM. In one embodiment, the effective concentration of the molecular beacon used in the methods of the invention is 200 nM.

A person skilled in the art would recognize that the effective concentration of the molecular beacons used in the methods and kits of the invention could be altered to yield an optimal signal-to-noise response, based on the source of cancerous cell and the particular purpose for which it is being used, all without departing from the scope of the invention. In one embodiment, the effective concentration of the molecular beacon used in the methods and kits of the invention would be a function of the label/quencher combination used, or in another embodiment, the disease type sought to be evaluated, or in another embodiment, the therapeutic agent used.

In another embodiment, the invention provides a method for detecting a polymorphism associated with target gene comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining the relative fluorescent intensity of said first and second detectable labels, whereby the relative intensities indicate the presence or absence of said polymorphism, thereby detecting said polymorphism. In another embodiment, the invention provides a method for detecting the expression level of a target gene comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining the fluorescent intensity of said first and second detectable labels, whereby the relative intensities indicate the expression level of said target gene, thereby detecting the expression level of said target gene.

The bimolecular beacon of the invention allows for the simple, sensitive, quantification of endogenous mRNA in living cells. In one embodiment, the invention allows for the study of endogenous gene expression under various conditions (e.g. environmental changes, therapeutic effects, etc.). In another embodiment, the invention allows for the study of gene expression in real-time, thus providing spatial and temporal resolution. In another embodiment, the invention is a tool for many laboratory scientists studying basic mechanisms of the cell.

In additional embodiments, the invention provides methods for detecting a subject nucleic acid, comprising combining the composition described herein with a sample suspected of containing a subject nucleic acid, and detecting hybridization by differential fluorescence intensities to determine the presence or absence, and/or the expression level of the subject nucleic acid in the sample in vitro or in vivo. In some preferred embodiments, the methods can be performed in vivo. Therefore, in a preferred embodiment of this method, the sample contains a living cell. The invention provides that the methods may be performed with samples comprising living tissues and cells that are taken out of the body, or that remain in situ.

The detection labels can be detected using a suitable detection mechanism known to one of skilled in the art and the detection can be quantified using a method known to one of skilled in the art.

In one embodiment, the detection of the first detectable label indicates a first value and the detection of said second detectable label indicates a second value. One embodiment, the relative difference between the first and second values indicates the presence or absence of a target gene or its polymorphism. In another embodiment, the relative difference between the first and second values indicates the level of expression of a target gene. The relative difference can be determined using a method known to one of skilled in the art.

In one embodiment, the cells used for the methods of the invention are obtained from a sample given by the subject. The sample to be analyzed may consist in one embodiment of, or comprise blood, sera, urine, feces, epidermal sample, skin sample, cheek swab, sperm, amniotic fluid, cultured cells, bone marrow sample and/or chorionic villi, and the like. A biological sample may be processed in another embodiment to release or otherwise make available a nucleic acid for detection as described herein. Such processing may include in one embodiment steps of nucleic acid manipulation, e.g., preparing a cDNA by reverse transcription of RNA from the biological sample. Thus, the nucleic acid to be amplified in one embodiment by the methods of the invention may be DNA or RNA.

The methods of the present invention further include detection of changes in the levels of expression of a nucleic acid target, or in RNA transcript, such that alterations of gene expression can be monitored as a result of the dose-dependent cellular response to external stimuli, such as drug molecules, hormones, growth factors, temperature, shear flow, or microgravity, for example. The invention further provides that the compositions can be used to visualize, i.e., through fluorescence or luminescence, the location and relative amount of gene expression in tissues and cells.

In diagnostic or prognostic detection methods the subject nucleic acid can comprise a genetic point mutation, deletion, or insertion relative to a naturally occurring or control nucleic acid. Such screening methods can permit the detection of the subject nucleic acid indicating the presence of a genetically associated disease, such as certain cancers, in the sample. There are many well-known examples of genetic mutations already in the art that are indicative of a disease state. The methods include the detection of nucleic acids comprising, for example, K-ras, survivin, p53, p16, DPC4, or BRCA2. The invention is not limited to a particular target gene. Any target gene can be detected by a bimolecular beacon that comprises a portion complementary to a portion of a target gene. Furthermore, the methods can be used to detect the amount of a subject nucleic acid being produced by an organism for purposes other than diagnosis or prognosis of a disease or condition.

In another embodiment, the invention provides a method for diagnosis of a disease in a subject comprising: providing a molecular beacon comprising a first nucleic acid operably linked to a first detectable label at one of its ends and a second nucleic acid operably linked to a second detectable label at its one end and a quencher at its other end; detecting said first and second detectable labels; and determining a relative fluorescent intensity of said first and second detectable labels, whereby the relative intensities indicate the presence of said disease in said subject, thereby diagnosing said disease.

In one embodiment, the invention provides for the simple, sensitive, quantification of endogenous mRNA for diagnostic applications. For example, the bimolecular beacon probe may be used to identify one cell with aberrant gene expression out of thousands.

In one embodiment, the bimolecular beacon of the invention provides for the development of therapeutics. In one embodiment, the bimolecular beacon can provide a fluorescent read-out of the effect of various therapeutics on the expression of the gene of interest. In another embodiment, the bimolecular beacon can allow for the quantification of gene expression in living subjects. This may allow for the early detection of disease, monitoring/development of therapeutics, the study of gene expression with temporal resolution in a natural environment.

The bimolecular beacon of the invention have use in nucleic acid detection, or amplification reactions as primers, or in the case of triamplification, blocking oligonucleotides, to detect or measure a nucleic acid product of the amplification, thereby detecting or measuring a target nucleic acid in a sample that is complementary to a 3' primer sequence. Accordingly, the beacons of the invention can be used in methods of diagnosis, wherein a sequence is complementary to a sequence (e.g., genomic) of an infectious disease agent, e.g. of human disease including but not limited to viruses, bacteria, parasites, and fungi, thereby diagnosing the presence of the infectious agent in a sample of nucleic acid from a patient. The target nucleic acid can be genomic or cDNA or mRNA or synthetic, human, animal, plant, yeast, or of a microorganism, etc.

In one embodiment, the invention provides a useful screening tool for drug discovery where a rapid specific and sensitive assay can detect in vivo changes in the expansion role of protein transcripts of interest, either at a steady state or in response to the administration of drug candidates. In another embodiment that can be used in the diagnosis or prognosis of a disease or disorder, the target sequence is a naturally occurring or wild type human genomic or RNA or cDNA sequence, mutation of which is implicated in the presence of a human disease or disorder, or alternatively, the target sequence can be the mutated sequence. In such an embodiment, optionally, the amplification reaction can be repeated for the same sample with different sets of probes that amplify, respectively, the naturally occurring sequence or the mutated version. By way of example, the mutation can be an insertion, substitution, and/or deletion of one or more nucleotides, or a translocation.

The invention further provides kits for the detection of a subject nucleic acid comprising the nucleic acid probe compositions described herein, necessary reagents and instructions for practicing the methods of detection. Such alternative compositions, methods and kits therefor are described in more detail by way of the examples, and still others will be apparent to one of skill in the art in view of the present disclosure.

In one embodiment, the kits of the invention may further comprises a positive and/or negative standard, wherein the standard can be assayed and compared to the test sample. It is to be understood that the kits of the invention may be modified and marketed for particular use.

In one embodiment, the kit of the invention may further comprise a software package contained on a computer storage medium, with a program for correlating values obtained with a standard, for storing and comparing, by date, or in another embodiment for extrapolating results obtained.

In the methods and kits according to embodiments of the present invention, data relating to values obtained for the parameters for malignant and non-malignant samples analyzed may be provided in a database such as Microsoft Access, Oracle, other SQL databases or simply in a data file. The database or data file may contain in one embodiment, a patient identifier such as a name or number, the values obtained, patient prognosis, age of onset of symptoms, therapy regimen, and other identifying and relevant characteristics, as will be understood by one skilled in the art. The database may contain, in other embodiments, the change in any of the parameters analyzed, as a function of time, or chemotherapy regimen, or a combination thereof. In one embodiment, the methods and kits of this invention may further comprise accessing a memory, or a means thereto for storing the obtained values for the parameters, and other data as described herein. In another embodiment, the methods of this invention may further comprise generating and graphically displaying the values obtained. In one embodiment, the analysis is executed by a processor or a virtual computer program.

In one embodiment the software incorporates statistical tools for determining the significance of the findings. Statistical significance is determined, in other embodiments, by conducting pairwise comparisons, and determining a p value. See, e.g., Dowdy and Wearden, Statistics for Research, John Wiley & Sons, New York, 1983. In one embodiment, a p value of 0.1, 0.05, 0.025, 0.02, 0.01, 0.005, 0.001, 0.0001, or less is indicative of a significant difference.

The term "about" as used herein means in quantitative terms plus or minus 5%, or in another embodiment plus or minus 10%, or in another embodiment plus or minus 15%, or in another embodiment plus or minus 20%.

As used herein, "subject" refers to a human or any other animal. A subject can be a patient, which refers to a human presenting to a medical provider for diagnosis or treatment of a disease. A human includes pre and post natal forms.

The following examples are presented in order to more fully illustrate the preferred embodiments of the invention. They should in no way be construed, however, as limiting the broad scope of the invention.

EXAMPLES

Example 1: Radiometric Bimolecular Beacons

The invention consists of an optical biosensor capable of accurately detecting nucleic acids in vitro and in living cells. The biosensor consists of two oligonucleotide-based probes that are hybridized to each other (FIG. 1A). One of the oligonucleotides forms a stem loop structure with one arm of the stem being significantly longer than the other. The shorter stem is labeled with a 'reporter' fluorophore. The overhanging (i.e. single stranded) portion of the longer stem is complementary to a second oligonucleotide that is labeled with a 'reference' fluorophore at one end and a quencher at the other. The quencher is held in close proximity to the 'reporter' fluorophore upon hybridization, while the 'reference' fluorophore is at the far end of the hybrid. The stem or the first oligonucleotide is of sufficient length to maintain a hairpin conformation; however, upon hybridization of the loop domain to a complementary nucleic acid target, the stem opens separating the 'reporter' fluorophore from the quencher resulting in a significant enhancement in fluorescence. In contrast, the signal from the 'reference' fluorophore is expected to be relatively unchanged upon hybridization. Although the mechanisms of activation of the 'reporter' fluorophore is similar to prior art (i.e. the conventional molecular beacon), this new probe has several additional and unique features. First, the longer double stranded domain drives nuclear export of the oligonucleotide-based probe. Second, the unquenched 'reference' fluorophore expands upon the utility of the probe by not only improving the ability to monitor transfection efficiency and (unbound) probe localization, but also provides a means for mRNA quantification. Specifically, ratiometric imaging, comparing the emission of the 'reporter' dye to the 'reference' dye, provides a simple means to quantify the extent of probe hybridization (i.e. mRNA levels). Ratiometric imaging also enhances the detection sensitivity by removing (through normalization) the impact of instrumental and experimental variability.

FIG. 1A illustrates the schematic of 'Ratiometric BiMolecular Beacons' (RBMBs) in the presence and absence of complementary target, according to one embodiment of the invention. As shown in FIG. 1A, RBMBs consist of two oligonucleotides that are hybridized together. One of the oligonucleotides forms a stem loop structure with one arm of the stem being significantly longer than the other. The shorter stem is labeled with a 'reporter' dye, depicted by a green circle in FIG. 1A. The longer stem is complementary to a second oligonucleotide that is labeled with a 'reference' dye (red circle) at one end and a quencher at the other (black circle). Formation of the bimolecular construct brings the quencher into close proximity to the 'reporter' dye, while the optically distinct 'reference' dye is held at the far end of the hybrid. The double stranded domain of the RBMB is designed to be of sufficient length such that the reference dye is not quenched (by the quencher) and the hybrid melting temperature is well above physiological temperature to ensure that the hybrid does not dissociate in cells. As shown in FIG. 1A, a 2-base (UU) single-stranded overhang has been added to the 3'-end of the double-stranded domain to facilitate nuclear export. The cellular mechanism responsible for the nuclear export of double-stranded RNA with a 3'-overhang is the same mechanism used by siRNA. Upon binding to a complementary nucleic acid target (shown in red), the reporter dye and quencher are forced apart and the reporter dye's fluorescence is restored. In contrast, the fluorescence emission of the reference dye is unaffected by hybridization.

Currently, the most widely used technology for imaging endogenous mRNA in living cells is the molecular beacon (i.e. hairpin forming oligonucleotide with a fluorophore at one end and a quencher at the other). Recently, several researchers have improved upon the use of molecular beacons by co-injecting the molecular beacon with a fluorescently labeled linear oligonucleotide and conducting ratiometric imaging to normalize variations in fluorescence; however, this approach generally requires microinjection to ensure both probes are present in equal quantities within each cell. The bimolecular beacons of the invention are not limited to microinjections since the reference dye and the reporter dye are coupled. Other specific advantages of our design include but are not limited to the ability to monitor transfection efficiency. Since the reference dye remains unquenched one can track whether it has been internalized and its intracellular localization. This will reduce false-negatives by allowing for the differentiation between untransfected cells and low levels of gene expression. Another advantage is an improved quantification of targeted of targeted mRNA by removing the instrumental and experimental variability. Yet another advantage is an improved quantification of mRNA over time by ensuring the ratio of 'reference' dye and 'reporter' dye remains constant over the course of the study. For ratiometric studies utilizing two independent oligonucleotides (e.g. molecular beacon and fluorescently labeled linear oligonucleotide) the intracellular lifetime and localization of each oligonucleotide may be different. Further advantage is an improved spatial quantification within single cells by ensuring that the reference dye and reporter dye co-localize. Additional advantage is an improved quantification from cell-to-cell by ensuring that an equal ratio of reference dye and reporter dye are present in each cell regardless of the method used to introduce the probe into the cell. Yet additional advantage is the ability to remove (via normalization) the cell-to-cell variations in fluorescence that may result from non-uniform transfection efficiency. The ability to have our probe exported from the nucleus is another advantage of the invention. A limitation of current molecular beacon designs is that they are rapidly sequestered into the nucleus upon introduction into living cells. Other advantages also exist.

Example 2: Evaluation of Radiometric Bimolecular Beacon Functionalities

Numerous studies have utilized molecular beacons (MBs) to image RNA expression in living cells; however, there is growing evidence that the sensitivity of RNA detection is significantly hampered by their propensity to emit false-positive signals. To overcome these and other limitations, the inventors of the instant application have developed a new RNA imaging probe called Ratiometric BiMolecular Beacon (RBMB), which combines functional elements of both conventional MBs and siRNA. Analogous to MBs, RBMBs elicit a fluorescent reporter signal upon hybridization to complementary RNA. In addition, an siRNA-like double-stranded domain is used to facilitate nuclear export. Accordingly, live-cell fluorescent imaging showed that RBMBs are localized predominantly in the cytoplasm, whereas MBs are sequestered into the nucleus. The retention of RBMBs within the cytoplasmic compartment led to more than a 15-fold reduction in false-positive signals and a significantly higher signal-to-background compared with MBs. The RBMBs were also designed to possess an optically distinct reference fluorophore that remains unquenched regardless of probe confirmation. This reference dye not only provided a means to track RBMB localization, but also allowed single cell measurements of RBMB fluorescence to be corrected for variations in probe delivery. Combined, these attributes enabled RBMBs to exhibit an improved sensitivity for RNA detection in living cells.

Materials and Methods

Cell Culture

MEF/3T3 cells were cultured in Dulbecco's MEM media supplemented with 1% Penn/Strep, 10% fetal bovine serum and incubated in 5% $CO_2$ at 37° C. Both Hela and MCF-7 cells were cultured in Eagle's minimum essential medium with 2 mM L-glutamine and Earle's BSS adjusted to contain 1.5 g/l sodium bicarbonate, 0.1 mM non-essential amino acids, 1 mM sodium pyruvate and 10% fetal bovine serum (FBS) in 5% $CO_2$ at 37° C. All cells were obtained from ATCC (Manassas, VA, USA). To generate cells that express Firefly luciferase, cells were infected with adenovirus, H4' 040CMVffLuciferase (Penn Genomic Center, Philadelphia, PA, USA), at a multiplicity of infection of $10^4$ particles per cell. Infection was carried out 24 hrs prior to delivery of RBMBs or MBs without any apparent loss of viability. Firefly activity was confirmed by making bioluminescent measurements on a Glomax 20/20 luminometer (Promega) following the administration of SteadyGlo (Promega). For comparison, cells infected with null adenovirus (H5.050CMVEmpty, Penn Genomic Center, Philadelphia, PA, USA) at a multiplicity of infection of $10^4$ particles per cell, were also prepared.

Synthesis and Design of RBMBs and Analogous MBs

Antisense firefly luciferase RBMBs and MBs were designed to hybridize to a targeting sequence (pGL3-Luc 235-252, Promega, Madison, WI, USA) that is not complementary to any known endogenous RNA target in mammalian cells. The RBMB consists of two 2'-O-methyl RNA oligonucleotides that are hybridized together. One of the oligonucleotides is labeled with a Cy5 (GE Life Sciences) reporter dye at the 5' end and has the sequence: /5Cy5/mGmUmCmAmCmCmUmCmAmGmCmGmUmA-mAmGmUmGmAmUmGmUmCmGmUmGmAmCmG-mAmCmGmGmCmAmGmCmGmUmGmCmAmGmCm UmCmUmU. The second oligonucleotide is labeled with an IRDye® 800 (Licor) reference dye at the 5' end and an Iowa Black® RQ-Sp quencher (IDT) at the 3' end, and has the sequence: /5IRD800/mGmAmGmCmUmGmCmAm-CmGmCmUmGmCmCmGmUmC/3UAbQSp/. For cytotoxicity assays and studies involving RBMB detection via flow cytometry, the second oligonucleotide was labeled with Alexa488 (Invitrogen) in place of IRDye® 800. To form RBMBs, equal molar ratios of the two oligonucleotides were allowed to hybridize in Phosphate Buffer (48 mM $K_2HPO_4$, 4.5 mM $KH_2PO_4$, 14 mM $NaH_2PO_4$), pH 7.2 at room temperature overnight. The resulting RBMBs were then purified from single-stranded oligonucleotides on a Superdex 30 prep grade column (GE healthcare) and concentrated on Microcon YM-10 centrifugal devices (10,000 MW cut-off; Millipore). The final concentration of the RBMBs was determined spectrophotometrically using a Cary 100 spectrophotometer (Varian). An analogous 2'-O-methyl RNA MB was synthesized with the sequence: /5Cy5/mGmUmC-mAmCmCmUmCmAmGmCmGmUmAmAmGmUmG-mAmUmGmUmCmG/iboT/mGmAmC/3IAbRQSp/. A luciferase RNA target with the sequence: UGGACAUCA-CUUACGCUGAGUA was also synthesized. All oligonucleotides were synthesized by Integrated DNA Technologies (IDT).

Optical Properties of RBMB

The emission profile of each RBMB was acquired on the FluoroMax-3 spectrofluorometer (Horiba Jobin Yvon) by setting the excitation wavelength to 647 nm for Cy5 and 780 nm for IRDye® 800. Emission scans from 655 nm to 800 nm and 790 nm to 850 nm were performed, respectively. These experiments were carried out in phosphate buffer, pH 7.2 using 250 nM RBMB in the presence or absence of 2.5 uM complementary RNA target.

Synthesis of Fluorescently Labeled Dextran

Aminodextran (MW: 10 kDa, Invitrogen) was dissolved in 50 mM Sodium Borate Buffer (pH 8) at a concentration of 10 mg/mL and reacted with 2.5 mM IRDye® 800-NHS ester (Li-Cor) at a dye to dextran molar ratio of 2.5 to 1. The fluorescently labeled dextrans were purified on NAP-5 gel chromatography columns (Amersham Biosciences) in Phosphate Buffer, pH 7.2. The concentration of the IRDye® 800 fluorophore was determined spectrophotometrically.

Cellular Delivery of RBMBs and MBs

Microporation was performed with an OneDrop MicroPorator (MP-100, BTX Harvard Apparatus) as per manufacturer's protocol. Specifically, cells were seeded in T-25 flasks in DMEM-FBS with no phenol red and no antibiotics 1 day prior to microporation. Before microporation, the cells were trypsinized, pelleted, and resuspended in media without phenol red and antibiotics, pelleted again, washed with 1×PBS, and resuspended in resuspension buffer R (BTX Harvard Apparatus) at a concentration of 120,000 cells per 11 µL. To deliver MBs into the cells, 1 µL of sample containing MBs and IRDye800-labeled dextran were added to the cells such that the final MB concentration and Alexa750-labeled dextran were 5 µM and 10 µM, respectively. To deliver RBMBs into cells, 1 µL of RBMBs were added to the cells such that the final concentration of RBMBs was also 5 µM. 10 µL of the cells (i.e. 100,000 cells) incubated in the presence of the probes were then microporated at 1500V with 3 pulses of 10 ms width for MEF-3T3 cells, at 990V with a single pulse of 50 ms width for MCF-7 cells, and at 1005V with 2 pulses of 35 ms width for Hela cells. Following microporation the cells were wash once in 1×PBS and resuspended in the DMEM (without Phenol red and supplemented with 10% FBS) and then seeded into the 8-well Lab-Tek Chambered Coverglass (155409, Nalge Nunc) or Glass bottom Dish (Willco Wells). Fluorescence images were acquired ~10 min (i.e. immediately after cell seeding), 1, 2, 3, 4, 5 and 24 hrs after microporation.

Cytotoxicity Assay

The effect of microporation on the viability of MEF-3T3, MCF-7 and HeLa cells was assessed via an MTT assay (ATCC) according to the manufacture's instructions. Absorbances (570 nm) were measured spectrophotometrically. Viability of cells was determined by dividing the absorbance measurements of the electroporated cells by the absorbance of cells that were not electroporated (0 V).

Transfection Efficiency

Following microporation of MEF-3T3, MCF-7 or HeLa cells in the presence of RBMBs with Alexa488 as the reference dye, the cells were washed once in PBS and analyzed on a Guava Excite flow cytometer fitted with a 488 nm excitation laser. Flow cytometry data was analyzed with FLOWJO (Version 7.2.2; Tree Star, Ashland, OR, USA). Fluorescence signal intensity was defined as the mean intensity of cells lying within a predefined gate. The appropriate gate was defined on an FSC versus SSC dot plot of cells that were not electroporated (0 V).

Fluorescent Microscopy

All microscopy images were performed on an Olympus IX 81 motorized inverted fluorescence microscope equipped with a back-illuminated EMCCD camera (Andor), an X-cite 120 excitation source (EXFO), and Sutter excitation and emission filter wheels. Images of Cy5 and IRDye® 800 were acquired using the filter sets (HQ620/60, HQ700/75, Q660LP) and (HQ710/75, HQ810/90, Q750LP) (Chroma). A LUC PLAN FLN 40× objective (NA 0.9) was used for all imaging studies. Results were analyzed with NIH Image J.

Ratiometric Analysis

Water-in-oil Emulsions: Emulsions containing MBs and fluorescently labeled dextrans or RBMBs were prepared as described previously. For each water-in-oil bubble, two images were acquired, one corresponding to the reporter dye (i.e. Cy5) and the other to the reference dye (i.e. IRDye® 800) on the dextran or RBMB. A region of interest (ROI) was drawn around each bubble, and the total fluorescent intensity was measured in each image. Similarly, the total fluorescence intensity from an ROI of equal size drawn around a "background" region was also measured for each image. The background subtracted fluorescence measurement for the reporter and the reference moiety was then calculated. The fluorescence ratio, $F_{rep}/F_{ref}$, was then calculated by dividing the background subtracted MB fluorescence by the background subtracted reference fluorescence.

Single cell analysis: Ratiometric analysis was performed on images of the cells using a method analogous to that used for water-in-oil emulsions, except the ROI was drawn around individual cells.

Analysis of RBMB/MB Nonspecific Opening

Procedures to determine the extent of MB nonspecific opening in living cells are well known in the art. In brief, the fluorescence ratio, $F_{rep}/F_{ref}$, was first determined for cell and microemulsion samples as described above. Then, the percent of MBs opened was calculated as follows:

$$\% \ MBs \ \text{Opened} = \frac{R_{CELL} - R_{BUBBLE,CLOSED}}{R_{BUBBLE,OPENED} - R_{BUBBLE,CLOSED}} \quad (1)$$

where $R_{CELL}$ is the fluorescence ratio, $F_{rep}/F_{ref}$, in living cells, and $R_{BUBBLES, CLOSED}$ and $R_{BUBBLES, OPENED}$ refer to the fluorescent ratio, $F_{rep}/F_{ref}$, for the unhybridized (fully quenched) and fully hybridized MBs, respectively, from the water-in-oil emulsions. The same study was also performed to quantify the extent of non-specific RBMB opening in living cells.

Functionality Assay

Aqueous samples containing 100 µM synthetic luciferase RNA targets in Phosphate Buffer, pH 7.2 were microinjected into cells containing MBs or RBMBs using a Femtojet and Injectman NI 2 (Eppendorf) microinjection system fitted with Femtotips I (Eppendorf). The targets were injected into cells at 24 hrs post-microporation. Fluorescent images of each cell were acquired immediately before and shortly after injection.

Analysis of RBMB and MB Hybridization Signal

In practice, MBs that are in a hairpin conformation still emit a low fluorescence background signal due to incomplete quenching of the fluorophore by the quencher. This means that the total MB signal emitted by a cell is the sum of the MB background signal and MB enhancement signal (i.e. due to hybridization and/or false-positive signals). Assuming the fluorescence ratio $F_{rep}/F_{ref}$ is the same in aqueous bubbles and in living cells, the contribution of MB background fluorescence to the total signal in cells can be calculated by the product of $F_{ref}$ and the fluorescent ratio of the aqueous bubble ($R_{BUBBLES, CLOSED}$). The MB enhancement signal can then be determined as the difference between the total integrated MB signal (MB$_{CELL}$) and the MB background signal in cells, as follows:

$$\text{MB Signal Enhancement} = \text{MB}_{CELL} - \text{REF}_{CELL} \cdot R_{BUBBLE,CLOSED} \quad (2)$$

Equation 2 was also applied to quantify the extent of RBMB and MB hybridization in living cells.

Results

Design and Characteristics of RBMBs.

Ratiometric BiMolecular Beacons (RBMBs) are composed of two hybridized oligonucleotides (FIG. 1A). One of the oligonucleotides forms a stem loop structure with one arm of the stem being significantly longer than the other. The shorter stem is labeled with a 'reporter' dye. The longer stem is complementary to a second oligonucleotide that is labeled with a 'reference' dye at one end and a quencher at the other, such that formation of the bimolecular construct brings the quencher into close proximity to the 'reporter' dye, while the optically distinct 'reference' dye is held at the far end of the hybrid. The double stranded domain of the RBMB is designed to be of sufficient length such that the reference dye does not interact with the quencher and the hybrid melting temperature is well above physiological temperature, to ensure that the hybrid does not dissociate in cells. A 2-base (UU) single-stranded overhang is included at the 3' end of the duplex to resemble the structure of siRNA.

Figure 1B:
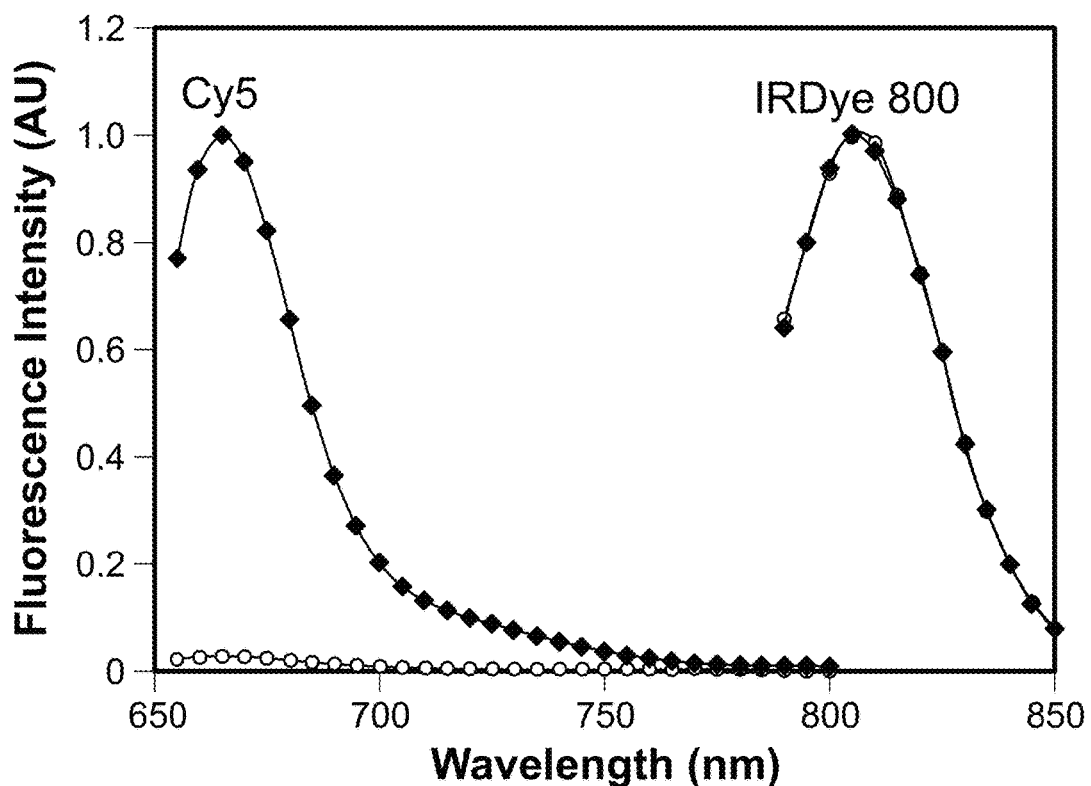

In this study, all RBMBs were synthesized with 2'-O-methyl RNA backbones, a Cy5 reporter dye and an Iowa Black RQ quencher. IRDye® 800 was used as the reference dye. The emission spectra of RBMBs in the presence and absence complementary RNA targets are shown in FIG. 1B. In the absence of target, the fluorescence emission of the Cy5 reporter dye was efficiently quenched, consistent with RBMBs assuming a hairpin conformation with the reporter dye and quencher being held in close proximity. Following the addition of complementary nucleic acid targets, there was >35-fold increase in reporter fluorescence. The mechanism responsible for the restoration of fluorescence is similar to that of conventional molecular beacons, with RNA hybridization driving the separation of the reporter dye and quencher. Since the distance between the reference dye, IRDye® 800, and quencher is unaffected by RBMB hybridization its fluorescence remained unchanged.

Intracellular Delivery, Localization and Biostability of RBMBs.

Figure 6A:
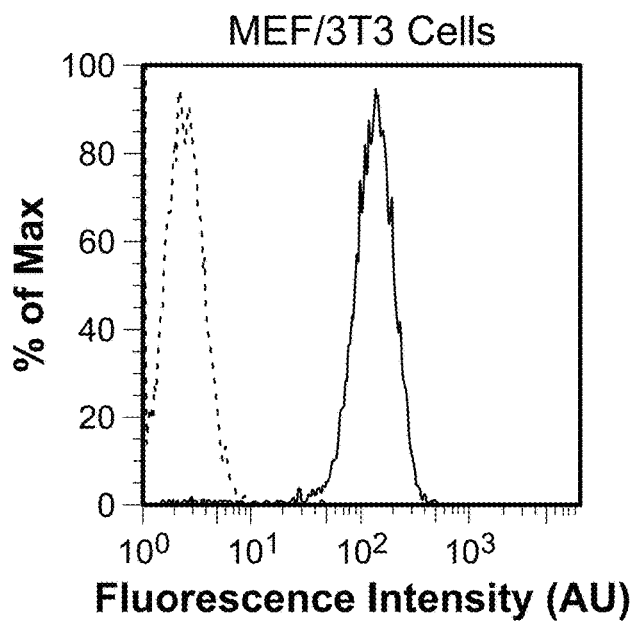
FIG. 6. Microporation delivery efficiency in (A) MEF/3T3, (B) HeLa, and (C) MCF-7 cells. Microporation exhibited a delivery efficiency of >98% for (A) MEF/3T3, (B) HeLa, and (C) MCF-7 cells.
Figure 6B:
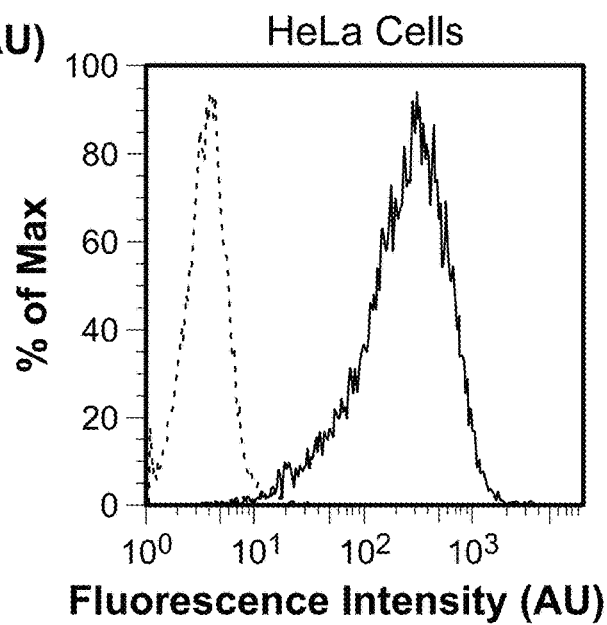
Figure 6C:
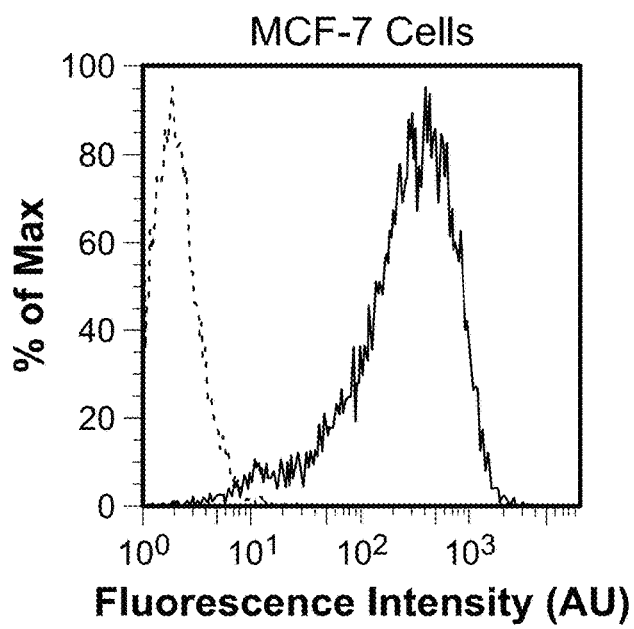

RBMBs were delivered into living cells via microporation. Microporation is a microliter-volume electroporation process that exhibits a reduction in the many harmful events often associated with electroporation, including heat generation, metal ion dissolution, pH variation, and oxide formation. Microporation exhibited a delivery efficiency of >98% for MEF/3T3, HeLa, and MCF-7 cells (see FIG. 6). To specifically test the effect of microporation on cell viability, an MTT cell proliferation assay was performed on each cell line. The viability was 97%±10%, 93%±11%, and 94%±2% for MEF/3T3, HeLa, and MCF-7 cells, respectively. These results show that microporation provides a very effective method for the delivery of RBMBs into living cells.

Figure 2A:
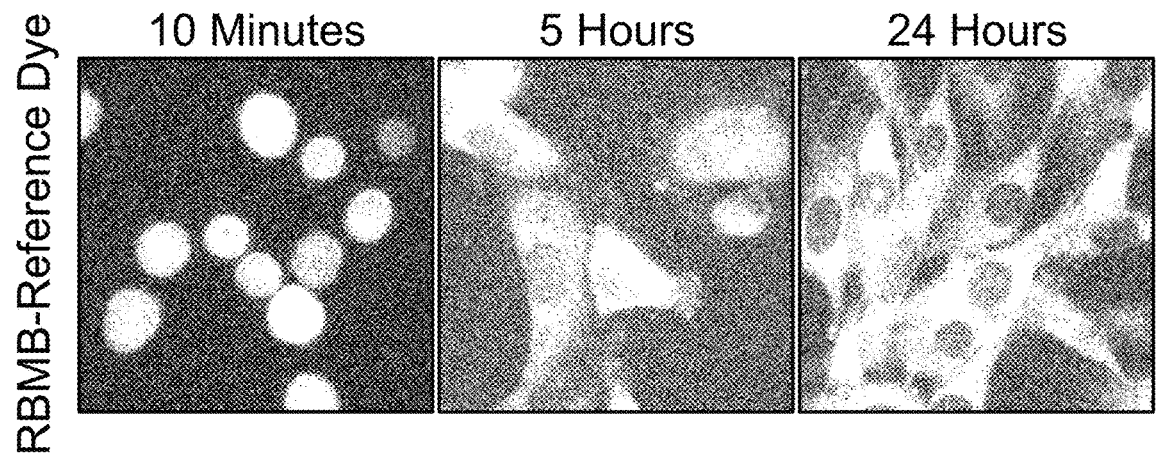
FIG. 2. Fluorescent images of MEF/3T3 cells at various times after microporation with nonsense molecular beacons (MBs) or RBMBs. (A) Images of the RBMB reference dye. (B) Images of the RBMB (top row) and conventional MB (bottom row) reporter dye. Representative fluorescence images are shown immediately following microporation (i.e. 10 mins) as well as 5 hrs and 24 hrs after microporation. The contrast for all images in (B) was adjusted simultaneously.

Following the delivery of RBMBs (or analogous MBs) into MEF/3T3, HeLa, or MCF-7 cells, the intracellular distribution was assessed by fluorescence microscopy. The targeting domain of both probes was chosen such that it was not complementary to any known endogenous RNAs. Therefore, it was expected that both probes would remain in a quenched state unless opened due to non-specific interactions and/or nuclease degradation. Approximately 10 minutes after microporation, the unquenched reference dye revealed that the RBMBs were distributed relatively uniformly throughout the cytoplasm and nucleus with, perhaps, a slight preference for the cytoplasm (FIG. 2A). By 5 hrs the RBMBs were predominantly localized within the cytoplasm. After 24 hrs, the RBMBs were still predominantly localized within the cytoplasm; however, there was a small amount of punctate fluorescence, presumably due to some uptake by lysosomes. Overall, these results show that incorporation of the siRNA-like structural elements into the RBMB design allowed for the efficient export of the RBMBs from the nucleus.

Figure 2B:
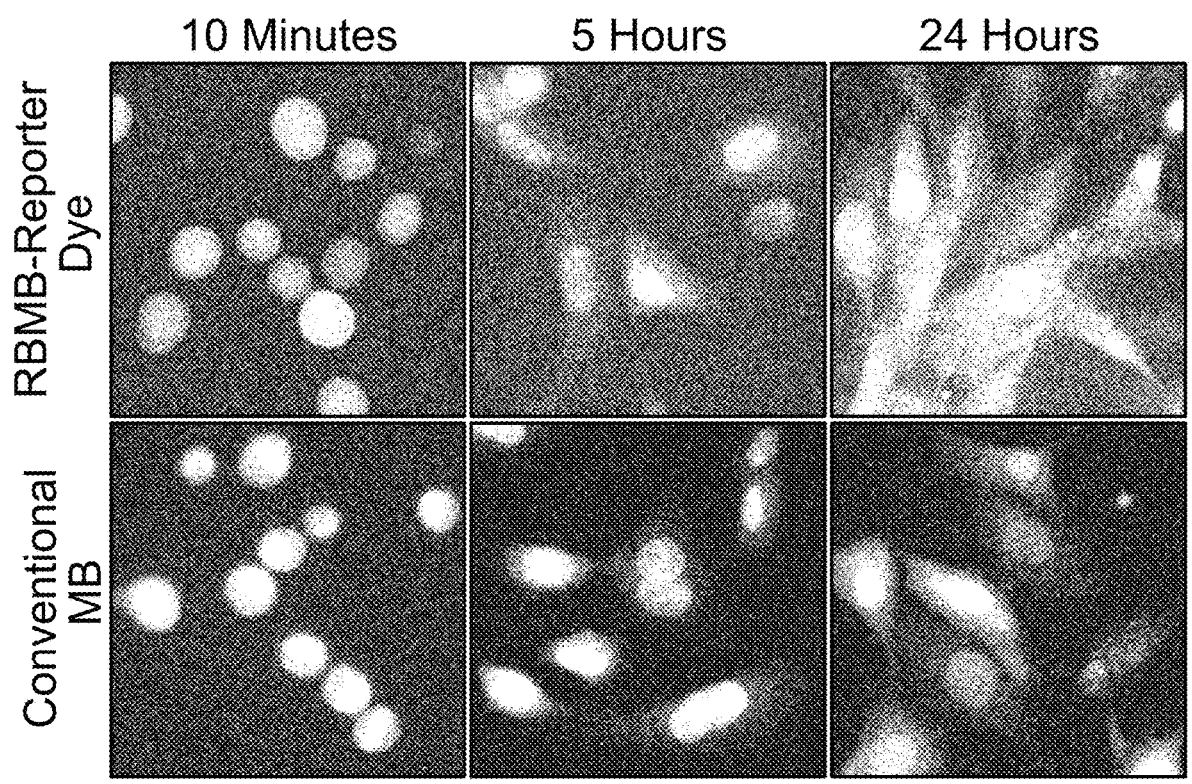

Fluorescent images of the RBMB reporter dye revealed that RBMB reporter fluorescence was well quenched for at least 24 hrs (FIG. 2B, top row). There was a faint fluorescent signal that could be observed in the nucleus of some cells, but overall the fluorescent signal within the cells was barely above background, indicating very effective quenching of the Cy5 reporter dye. Conversely, conventional MBs elicited a bright fluorescent signal within the nucleus within 10 minutes of being microporated into cells (FIG. 2B, bottom row). Only a faint fluorescent signal was observed in the cytoplasm. This pattern remained similar for at least 24 hrs, although the overall fluorescent intensity of the MBs did appear to increase with time. These results show that while RBMBs exhibit very little non-specific opening, conventional MBs exhibit a significant extent of non-specific opening, primarily within the nucleus of living cells.

To quantify the extent of RBMB nonspecific opening, the fluorescent ratio (i.e. total integrated reporter fluorescence/total integrated reference fluorescence, $F_{rep}/F_{ref}$), was compared with fluorescence microscopy measurements of the same RBMB samples prior to intracellular delivery. Specifically, water-in-oil emulsions were prepared with the RBMB samples in the absence and presence of target, representing 0% and 100% opening of the RBMBs, respectively. Images of the fluorescent bubbles were then acquired directly on the microscope and the ratio, $F_{rep}/F_{ref}$, was calculated. Using these extracellular measurements as standards, the percent of open RBMBs within living cells was determined. A similar analysis was conducted with conventional MBs in the presence of dextran (10 kDa) labeled with IRDye® 800.

Figure 3A:
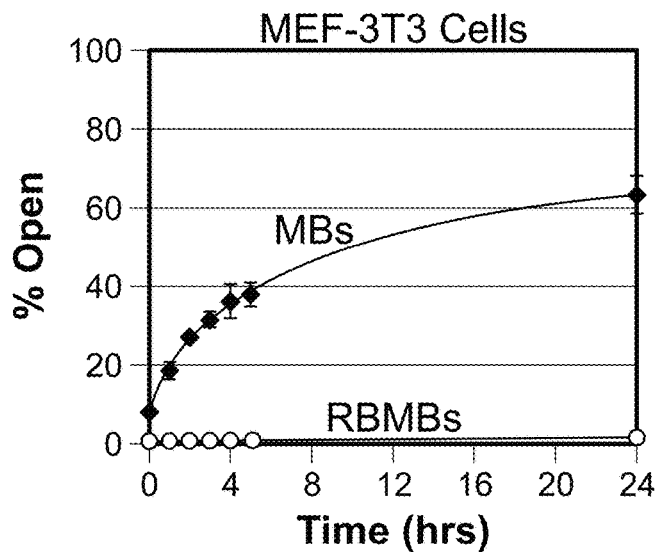
FIG. 3. Quantitative analysis of non-specific MB and RBMB opening in living cells. Nonsense MBs (♦) and RBMBs (○) were microporated into (A) MEF/3T3, (B) HeLa and (C) MCF-7 cells and the percent non-specific opening was quantified over the course of 24 hours. Each data point represents the mean and standard deviation from at least 50 cells.
Figure 3B:
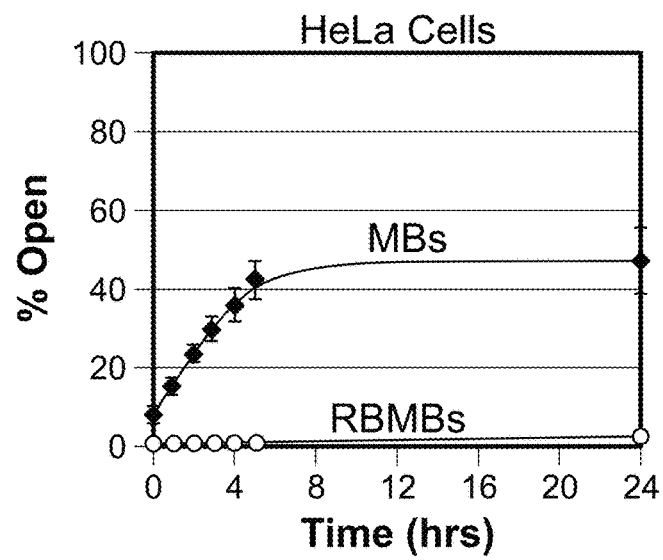
Figure 3C:
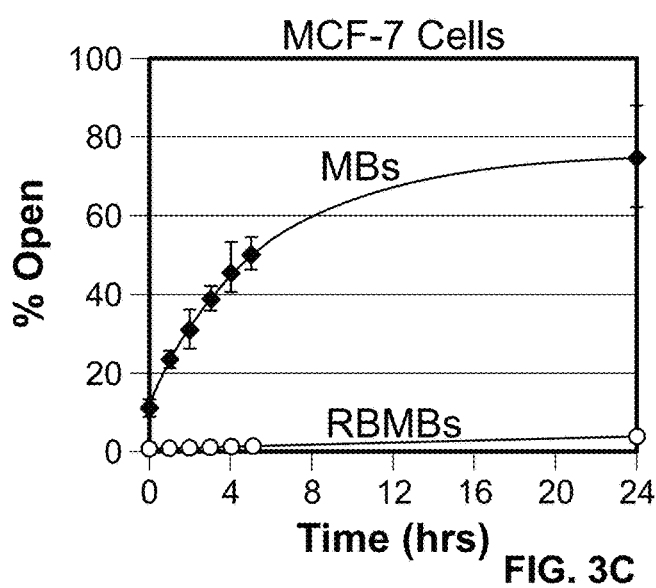

Interestingly, ratiometric analysis revealed that less than 1% of the RBMBs were opened non-specifically in MEF/3T3 cells 5 hrs after microporation. Further, only 1.2% of the RBMBs were open after 24 hrs (FIG. 3A). In contrast, the MBs actually exhibited a very significant amount of non-specific opening following microporation (FIG. 3A). Approximately 8% of the MBs were opened within 10 minutes following microporation into MEF/3T3 cells and by 24 hrs nearly 63% of the MBs were open. Similar results were obtained when RBMBs and MBs were introduced into HeLa and MCF-7 cells (FIG. 3B-C). Overall, these results demonstrate that RBMBs are far more resistant to nonspecific opening in living cells than conventional MBs.

Functional Analysis of RBMBs in Living Cells.

Figure 4A:
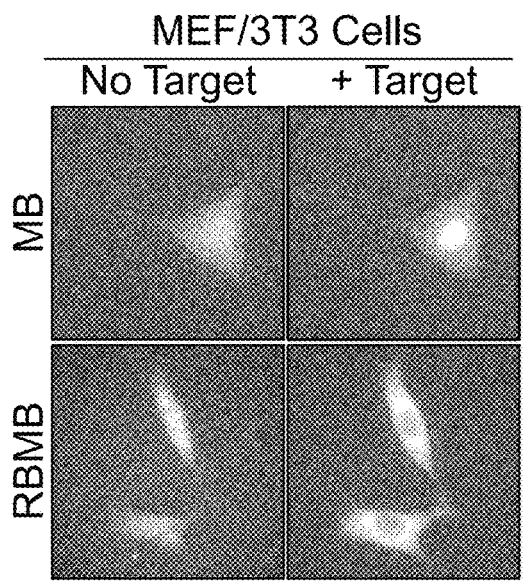
FIG. 4. Functional analysis of MBs and RBMBs in living cells. Twenty-four hours following the microporation of MBs or RBMBs into (A) MEF/3T3, (B) HeLa, and (C) MCF-7 cells, excess complementary RNA targets were microinjected into the cytoplasm. Fluorescent images of the cells were acquired immediately before and several minutes after microinjection. Representative fluorescent images are shown.
Figure 4B:
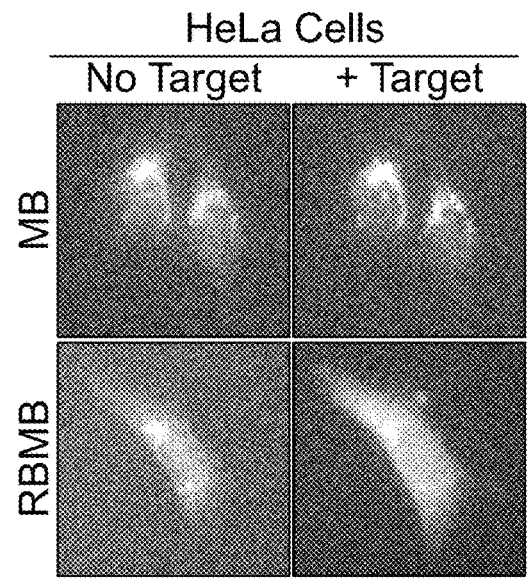
Figure 4C:
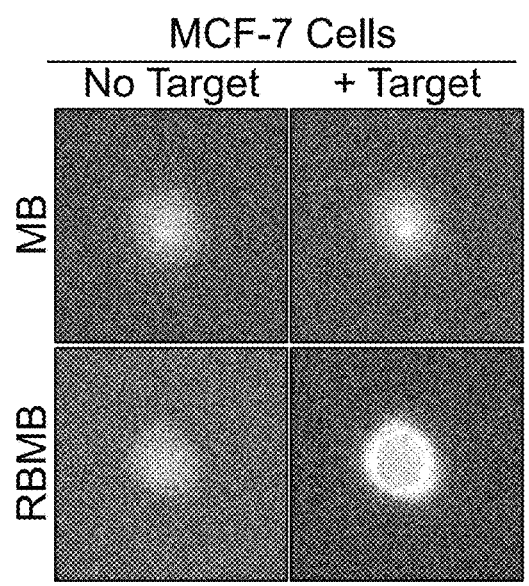

To assess the functionality of RBMBs and MBs following delivery into live cells, excess complementary RNA targets were microinjected into the cytosol of single cells 24 hrs after microporation. Fluorescent images were acquired immediately before and shortly after microinjection. Representative images of MEF/3T3 cells are shown in FIG. 4A. While cells with MBs exhibited little to no enhancement in fluorescence following injection of nucleic acid targets, cells with RBMBs exhibited a substantial enhancement in fluorescence. Quantitative analysis of cellular fluorescence before and after the injection of RNA targets revealed that RBMBs exhibited a signal enhancement (i.e. signal-to-background, S:B) of 9.0±2.4. In contrast, conventional MBs exhibited a S:B of only 1.12±0.07. Similar observations were made for HeLa and MCF-7 cells (FIG. 4B-C). Specifically, RBMBs exhibited a S:B of 9.9±3.2 and 15.3±3.3 in Hela and MCF-7 cells, respectively, while conventional MBs exhibited a S:B of less than 1.25 for both cell lines. These results show that far more RBMBs are functionally active after 24 hrs compared with MBs. Overall, these results show that RBMBs may be utilized for the long-term monitoring of gene expression.

Sensitivity of RBMBs for Intracellular RNA Detection.

Figure 5A:
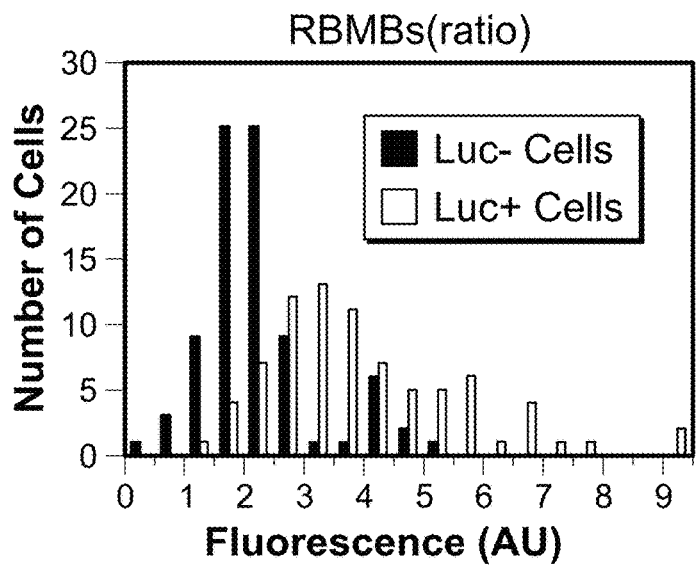
FIG. 5. Intracellular RNA detection using MBs and RBMBs. (A) Luc+ and luc− MEF/3T3 cells were microporated in the presence of antisense luciferase RBMBs. Fluorescence measurements of single living cells were acquired 3-5 hours after microporation and fluorescence intensity histograms were constructed. Measurements of the reference dye were used to correct for cell-to-cell variations in reporter fluorescence owing to inhomogeneities in probe delivery. (B) Fluorescence intensity histograms of RBMB fluorescence in luc+ and luc− cells, for same cells analyzed in 'A', but fluorescence measurements were not adjusted for inhomogeneities in probe delivery. (C) Fluorescence intensity histograms of MB fluorescence in luc+ and luc− cells. MBs were microporated into MEF/3T3 cells in the presence of fluorescently-labeled (IRDye® 800) dextran. The IRDye® 800 signal was used to correct for cell-to-cell variations in reporter fluorescence owing to inhomogeneities in probe delivery. At least 80 cells were analyzed for each experimental condition.
Figure 5B:
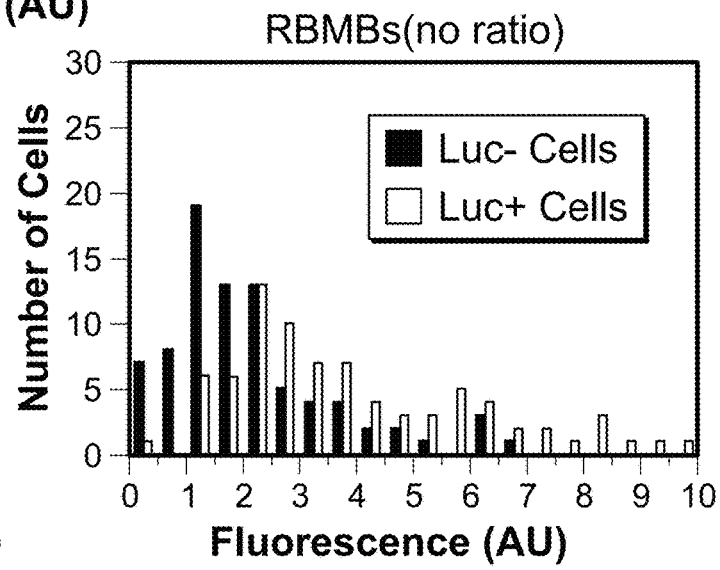

To confirm that RBMBs could be used to detect gene expression in single living cells, antisense luciferase RBMBs were delivered into MEF/3T3 cells that express Firefly luciferase (luc+). Cells that did not express Firefly luciferase (luc−) were used as a negative control. FIG. 5A shows the fluorescence intensity histograms of cells that were imaged 3-5 hrs after microporation. The mean fluorescent intensity was 150% higher in luc+ cells than in the luc− cells ($P<0.0001$). It should be noted that measurements of the reference dye were used to correct for cell-to-cell variations in reporter fluorescence owing to inhomogeneities in probe delivery. When ratiometric imaging approaches were not applied, the mean fluorescent intensity was only 64% higher in luc+ cells than in luc− cells ($P<0.001$) (FIG. 5B). Therefore, ratiometric measurements led to >2.3-fold improvement in sensitivity. Even when ratiometric imaging was employed, the total enhancement in fluorescence in luc+ cells was only a small fraction of the full dynamic range of RBMBs.

Figure 5C:
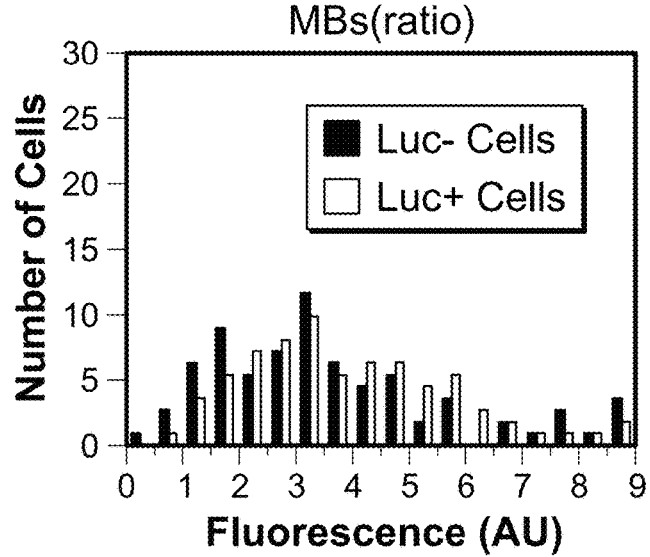

To confirm the hypothesis that RBMBs would exhibit an improvement in the sensitivity of RNA detection compared with analogous MBs, antisense luciferase MBs were delivered into luc+ and luc− MEF/3T3 cells and cellular fluorescence was quantified (FIG. 5C). Results indicated that MBs exhibited similar mean fluorescence intensities in both luc+ and luc− cells ($P=0.476$). Overall, these results clearly underline the advantages of RBMBs for live-cell RNA detection.

In summary, the inventors of the instant application have developed a new RNA imaging probe, RBMB, that exhibits high resistance to nonspecific opening, high sensitivity for RNA detection, and prolonged functionality in living cells. Nuclear sequestration and false-positive signals were avoided by incorporating a structural element that resembles siRNA into the probe design. Further, incorporation of an unquenched, optically distinct reference dye allowed single cell measurements of RBMB fluorescence to be corrected for variations in probe delivery. Combined, these attributes enabled RBMBs to detect lower levels of RNA expression than could be detected by conventional MBs. The improved sensitivity of RBMBs will allow live cell RNA imaging approaches to be utilized for a much wider range of applications than previously possible.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A free-floating bimolecular beacon for nucleic acid detection, comprising:
    a first detectable label, a second detectable label, and a quencher;
    a first nucleic acid 30 to 100 nucleotides in length; and
    a second nucleic acid 10 to 50 nucleotides in length;
    wherein said first nucleic acid is longer than said second nucleic acid,
    wherein said first nucleic acid forms a stem-loop structure with a loop 10 to 50 nucleotides in length and with a first arm and a second arm, wherein the second arm forms a double-helical region with the first arm by base pairing, wherein the first arm is longer than the second arm and forms an overhanging portion of at least 10 nucleotides, and wherein said loop contains a contiguous sequence complementary to at least 10 consecutive nucleotides of a nucleic acid sequence of interest;
    wherein said second nucleic acid is complementary to and forms a double-stranded stem hybrid with the overhanging portion of said first nucleic acid, and wherein the second nucleic acid has an end proximal to the second arm of the first nucleic acid and an end distal to the second arm of the first nucleic acid,
    wherein the double-stranded stem hybrid at its end distal from the stem loop has a two base single-stranded 3'-overhang with a sequence of UU,
    wherein the second arm of the first nucleic acid is operably linked at its end to the first detectable label or to the quencher, wherein the second nucleic acid at the end proximal to the second arm of the first nucleic acid is operably linked to the quencher or to the first detectable label, respectively, wherein the first nucleic acid or the second nucleic acid is operably linked to the second detectable label at an unlabeled end of the first or second nucleic acid, and wherein the first detectable label is a first fluorophore, the second detectable label is a second fluorophore that is optically distinct from the first fluorophore, and the quencher quenches fluorescence from the first fluorophore by resonance energy transfer.

2. The molecular beacon of claim 1, wherein the detection of said first detectable label indicates a first value and the detection of said second detectable label indicates a second value.

3. The molecular beacon of claim 1, wherein said quencher does not interact with said second detectable label.

4. The molecular beacon of claim 1, wherein said quencher quenches the activity of said first detectable label when both first and second nucleic acids are hybridized to each other to form a stem hybrid, and wherein said quencher does not quench the activity of said first detectable label when the first nucleic acid is hybridized to the nucleic acid sequence of interest.

5. The molecular beacon of claim 1, wherein said resonance energy transfer is fluorescence resonance energy transfer.

6. The molecular beacon of claim 1, wherein said resonance energy transfer is luminescence resonance energy transfer.

7. The molecular beacon of claim 1, wherein said first or second detectable label is an organic dye, a photoluminescent dye, a fluorophore, Cy3, Cy5, ROX, Texas Red, a phycobiliprotein, Red Phycoerythrin (RPE), Blue Phycoerythrin (BPE), Allophycocyanin (APC), BCPDA, BHHCT, Isocyanato-EDTA, Quantum Dye, a lanthanide chelator molecule, DTPA-cytosine, DTPA-cs124, BCPDA, BHHCT, Isocyanato-EDTA or W1024.

8. The molecular beacon of claim 1, wherein said first or second detectable label is conjugated to said first or second nucleic acid via a covalent bond or an affinity bond.

9. The molecular beacon of claim 1, wherein said quencher comprises tetra-methylcarboxyrhodamine (TAMRA) or 4-(4-dimethylaminophenylazo)benzoic acid ("DABCYL").

10. A free-floating bimolecular beacon for nucleic acid detection, comprising:
  a detectable label and a quencher;
  a first nucleic acid 30 to 100 nucleotides in length; and
  a second nucleic acid 10 to 50 nucleotides in length,
  wherein said first nucleic acid is longer than said second nucleic acid,
  wherein said first nucleic acid forms a stem-loop structure with a loop 10 to 50 nucleotides in length and with a first arm and a second arm, wherein the second arm forms a double-helical region with the first arm by base pairing, wherein the first arm is longer than the second arm to form an overhanging portion of at least 10 nucleotides, and wherein said loop contains a contiguous sequence complementary to at least 10 consecutive nucleotides of a nucleic acid sequence of interest;
  wherein said second nucleic acid is complementary to and forms a double-stranded stem hybrid with the overhanging portion of said first nucleic acid, and wherein the second nucleic acid has an end proximal to the second arm of the first nucleic acid and an end distal to the second arm of the first nucleic acid,
  wherein the double-stranded stem hybrid at its end distal from the stem loop has a two base single-stranded 3'-overhang with a sequence of UU,
  wherein the second arm of the first nucleic acid is operably linked at its end to the detectable label or to the quencher, and
  wherein the second nucleic acid at the end proximal to the second arm of the first nucleic acid is operably linked to the quencher or the detectable label, respectively, and
  wherein said detectable label is a fluorophore and said quencher quenches fluorescence from the fluorophore by resonance energy transfer.

\* \* \* \* \*

SEQUENCE LISTING

```
<160> NUMBER OF SEQ ID NOS: 4

<210> SEQ ID NO 1
<211> LENGTH: 22
<212> TYPE: RNA
<213> ORGANISM: Firefly

<400> SEQUENCE: 1
uggacaucac uuacgcugag ua                                              22

<210> SEQ ID NO 2
<211> LENGTH: 48
<212> TYPE: RNA
<213> ORGANISM: Firefly
<220> FEATURE:
<221> NAME/KEY: modified_base
<222> LOCATION: (1)..(1)
<223> OTHER INFORMATION: 2'-O-methylguanosine
<220> FEATURE:
<221> NAME/KEY: modified_base
<222> LOCATION: (2)..(2)
<223> OTHER INFORMATION: 2'-O-methyluridine
<220> FEATURE:
<221> NAME/KEY: modified_base
<222> LOCATION: (3)..(3)
<223> OTHER INFORMATION: 2'-O-methylcytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-O-methylcytidine
<220> FEATURE:
<221> NAME/KEY: modified_base
```

```
<222> LOCATION: (6)..(6)
<223> OTHER INFORMATION: 2'-O-methylcytidine
<220> FEATURE:
<221> NAME/KEY: modified_base
<222> LOCATION: (7)..(7)
<223> OTHER INFORMATION: 2'-O-methyluridine
<220> FEATURE:
<221> NAME/KEY: modified_base
<222> LOCATION: (8)..(8)
<223> OTHER INFORMATION: 2'-O-methylcytidine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: 2'-O-methylguanosine
<220> FEATURE:
<221> NAME/KEY: modified_base
<222> LOCATION: (11)..(11)
<223> OTHER INFORMATION: 2'-O-methylcytidine
<220> FEATURE:
<221> NAME/KEY: modified_base
<222> LOCATION: (12)..(12)
<223> OTHER INFORMATION: 2'-O-methylguanosine
<220> FEATURE:
<221> NAME/KEY: modified_base
<222> LOCATION: (13)..(13)
<223> OTHER INFORMATION: 2'-O-methyluridine
<220> FEATURE:
<221> NAME/KEY: modified_base
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methylguanosine
<220> FEATURE:
<221> NAME/KEY: modified_base
<222> LOCATION: (17)..(17)
<223> OTHER INFORMATION: 2'-O-methyluridine
<220> FEATURE:
<221> NAME/KEY: modified_base
<222> LOCATION: (18)..(18)
<223> OTHER INFORMATION: 2'-O-methylguanosine
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O-methyluridine
<220> FEATURE:
<221> NAME/KEY: modified_base
<222> LOCATION: (21)..(21)
<223> OTHER INFORMATION: 2'-O-methylguanosine
<220> FEATURE:
<221> NAME/KEY: modified_base
<222> LOCATION: (22)..(22)
<223> OTHER INFORMATION: 2'-O-methyluridine
<220> FEATURE:
<221> NAME/KEY: modified_base
<222> LOCATION: (23)..(23)
<223> OTHER INFORMATION: 2'-O-methylcytidine
<220> FEATURE:
<221> NAME/KEY: modified_base
<222> LOCATION: (24)..(24)
<223> OTHER INFORMATION: 2'-O-methylguanosine
<220> FEATURE:
<221> NAME/KEY: modified_base
<222> LOCATION: (25)..(25)
<223> OTHER INFORMATION: 2'-O-methyluridine
<220> FEATURE:
```

```
<221> NAME/KEY: modified_base
<222> LOCATION: (26)..(26)
<223> OTHER INFORMATION: 2'-O-methylguanosine
<220> FEATURE:
<221> NAME/KEY: modified_base
<222> LOCATION: (27)..(27)
<223> OTHER INFORMATION: 2'-O-methyladenosine
<220> FEATURE:
<221> NAME/KEY: modified_base
<222> LOCATION: (28)..(28)
<223> OTHER INFORMATION: 2'-O-methylcytidine
<220> FEATURE:
<221> NAME/KEY: modified_base
<222> LOCATION: (29)..(29)
<223> OTHER INFORMATION: 2'-O-methylguanosine
<220> FEATURE:
<221> NAME/KEY: modified_base
<222> LOCATION: (30)..(30)
<223> OTHER INFORMATION: 2'-O-methyladenosine
<220> FEATURE:
<221> NAME/KEY: modified_base
<222> LOCATION: (31)..(31)
<223> OTHER INFORMATION: 2'-O-methylcytidine
<220> FEATURE:
<221> NAME/KEY: modified_base
<222> LOCATION: (32)..(32)
<223> OTHER INFORMATION: 2'-O-methylguanosine
<220> FEATURE:
<221> NAME/KEY: modified_base
<222> LOCATION: (33)..(33)
<223> OTHER INFORMATION: 2'-O-methylguanosine
<220> FEATURE:
<221> NAME/KEY: modified_base
<222> LOCATION: (34)..(34)
<223> OTHER INFORMATION: 2'-O-methylcytidine
<220> FEATURE:
<221> NAME/KEY: modified_base
<222> LOCATION: (35)..(35)
<223> OTHER INFORMATION: 2'-O-methyladenosine
<220> FEATURE:
<221> NAME/KEY: modified_base
<222> LOCATION: (36)..(36)
<223> OTHER INFORMATION: 2'-O-methylguanosine
<220> FEATURE:
<221> NAME/KEY: modified_base
<222> LOCATION: (37)..(37)
<223> OTHER INFORMATION: 2'-O-methylcytidine
<220> FEATURE:
<221> NAME/KEY: modified_base
<222> LOCATION: (38)..(38)
<223> OTHER INFORMATION: 2'-O-methylguanosine
<220> FEATURE:
<221> NAME/KEY: modified_base
<222> LOCATION: (39)..(39)
<223> OTHER INFORMATION: 2'-O-methyluridine
<220> FEATURE:
<221> NAME/KEY: modified_base
<222> LOCATION: (40)..(40)
<223> OTHER INFORMATION: 2'-O-methylguanosine
<220> FEATURE:
<221> NAME/KEY: modified_base
<222> LOCATION: (41)..(41)
<223> OTHER INFORMATION: 2'-O-methylcytidine
<220> FEATURE:
<221> NAME/KEY: modified_base
<222> LOCATION: (42)..(42)
<223> OTHER INFORMATION: 2'-O-methyladenosine
<220> FEATURE:
<221> NAME/KEY: modified_base
<222> LOCATION: (43)..(43)
<223> OTHER INFORMATION: 2'-O-methylguanosine
<220> FEATURE:
<221> NAME/KEY: modified_base
<222> LOCATION: (44)..(44)
<223> OTHER INFORMATION: 2'-O-methylcytidine
<220> FEATURE:
<221> NAME/KEY: modified_base
<222> LOCATION: (45)..(45)
<223> OTHER INFORMATION: 2'-O-methyluridine
```

```
<220> FEATURE:
<221> NAME/KEY: modified_base
<222> LOCATION: (46)..(46)
<223> OTHER INFORMATION: 2'-O-methylcytidine
<220> FEATURE:
<221> NAME/KEY: modified_base
<222> LOCATION: (47)..(47)
<223> OTHER INFORMATION: 2'-O-methyluridine
<220> FEATURE:
<221> NAME/KEY: modified_base
<222> LOCATION: (48)..(48)
<223> OTHER INFORMATION: 2'-O-methyluridine

<400> SEQUENCE: 2
gucaccucag cguaagugau gucgugacga cggcagcgug cagcucuu                48

<210> SEQ ID NO 3
<211> LENGTH: 18
<212> TYPE: RNA
<213> ORGANISM: Firefly
<220> FEATURE:
<221> NAME/KEY: modified_base
<222> LOCATION: (1)..(1)
<223> OTHER INFORMATION: 2'-O-methylguanosine
<220> FEATURE:
<221> NAME/KEY: modified_base
<222> LOCATION: (2)..(2)
<223> OTHER INFORMATION: 2'-O-methyladenosine
<220> FEATURE:
<221> NAME/KEY: modified_base
<222> LOCATION: (3)..(3)
<223> OTHER INFORMATION: 2'-O-methylguanosine
<220> FEATURE:
<221> NAME/KEY: modified_base
<222> LOCATION: (4)..(4)
<223> OTHER INFORMATION: 2'-O-methylcytidine
<220> FEATURE:
<221> NAME/KEY: modified_base
<222> LOCATION: (5)..(5)
<223> OTHER INFORMATION: 2'-O-methyluridine
<220> FEATURE:
<221> NAME/KEY: modified_base
<222> LOCATION: (6)..(6)
<223> OTHER INFORMATION: 2'-O-methylguanosine
<220> FEATURE:
<221> NAME/KEY: modified_base
<222> LOCATION: (7)..(7)
<223> OTHER INFORMATION: 2'-O-methylcytidine
<220> FEATURE:
<221> NAME/KEY: modified_base
<222> LOCATION: (8)..(8)
<223> OTHER INFORMATION: 2'-O-methyladenosine
<220> FEATURE:
<221> NAME/KEY: modified_base
<222> LOCATION: (9)..(9)
<223> OTHER INFORMATION: 2'-O-methylcytidine
<220> FEATURE:
<221> NAME/KEY: modified_base
<222> LOCATION: (10)..(10)
<223> OTHER INFORMATION: 2'-O-methylguanosine
<220> FEATURE:
<221> NAME/KEY: modified_base
<222> LOCATION: (11)..(11)
<223> OTHER INFORMATION: 2'-O-methylcytidine
<220> FEATURE:
<221> NAME/KEY: modified_base
<222> LOCATION: (12)..(12)
<223> OTHER INFORMATION: 2'-O-methyluridine
<220> FEATURE:
<221> NAME/KEY: modified_base
<222> LOCATION: (13)..(13)
<223> OTHER INFORMATION: 2'-O-methylguanosine
<220> FEATURE:
<221> NAME/KEY: modified_base
<222> LOCATION: (14)..(14)
<223> OTHER INFORMATION: 2'-O-methylcytidine
<220> FEATURE:
```

```
<221> NAME/KEY: modified_base
<222> LOCATION: (15)..(15)
<223> OTHER INFORMATION: 2'-O-methylcytidine
<220> FEATURE:
<221> NAME/KEY: modified_base
<222> LOCATION: (16)..(16)
<223> OTHER INFORMATION: 2'-O-methylguanosine
<220> FEATURE:
<221> NAME/KEY: modified_base
<222> LOCATION: (17)..(17)
<223> OTHER INFORMATION: 2'-O-methyluridine
<220> FEATURE:
<221> NAME/KEY: modified_base
<222> LOCATION: (18)..(18)
<223> OTHER INFORMATION: 2'-O-methylcytidine

<400> SEQUENCE: 3
gagcugcacg cugccguc                                                 18

<210> SEQ ID NO 4
<211> LENGTH: 28
<212> TYPE: DNA
<213> ORGANISM: Firefly
<220> FEATURE:
<221> NAME/KEY: modified_base
<222> LOCATION: (1)..(1)
<223> OTHER INFORMATION: 2'-O-methylguanosine
<220> FEATURE:
<221> NAME/KEY: modified_base
<222> LOCATION: (2)..(2)
<223> OTHER INFORMATION: 2'-O-methyluridine
<220> FEATURE:
<221> NAME/KEY: modified_base
<222> LOCATION: (3)..(3)
<223> OTHER INFORMATION: 2'-O-methylcytidine
<220> FEATURE:
<221> NAME/KEY: modified_base
<222> LOCATION: (4)..(4)
<223> OTHER INFORMATION: 2'-O-methyladenosine
<220> FEATURE:
<221> NAME/KEY: modified_base
<222> LOCATION: (5)..(5)
<223> OTHER INFORMATION: 2'-O-methylcytidine
<220> FEATURE:
<221> NAME/KEY: modified_base
<222> LOCATION: (6)..(6)
<223> OTHER INFORMATION: 2'-O-methylcytidine
<220> FEATURE:
<221> NAME/KEY: modified_base
<222> LOCATION: (7)..(7)
<223> OTHER INFORMATION: 2'-O-methyluridine
<220> FEATURE:
<221> NAME/KEY: modified_base
<222> LOCATION: (8)..(8)
<223> OTHER INFORMATION: 2'-O-methylcytidine
<220> FEATURE:
<221> NAME/KEY: modified_base
<222> LOCATION: (9)..(9)
<223> OTHER INFORMATION: 2'-O-methyladenosine
<220> FEATURE:
<221> NAME/KEY: modified_base
<222> LOCATION: (10)..(10)
<223> OTHER INFORMATION: 2'-O-methylguanosine
<220> FEATURE:
<221> NAME/KEY: modified_base
<222> LOCATION: (11)..(11)
<223> OTHER INFORMATION: 2'-O-methylcytidine
<220> FEATURE:
<221> NAME/KEY: modified_base
<222> LOCATION: (12)..(12)
<223> OTHER INFORMATION: 2'-O-methylguanosine
<220> FEATURE:
<221> NAME/KEY: modified_base
<222> LOCATION: (13)..(13)
<223> OTHER INFORMATION: 2'-O-methyluridine
<220> FEATURE:
<221> NAME/KEY: modified_base
```

```
<222> LOCATION: (14)..(14)
<223> OTHER INFORMATION: 2'-O-methyladenosine
<220> FEATURE:
<221> NAME/KEY: modified_base
<222> LOCATION: (15)..(15)
<223> OTHER INFORMATION: 2'-O-methyladenosine
<220> FEATURE:
<221> NAME/KEY: modified_base
<222> LOCATION: (16)..(16)
<223> OTHER INFORMATION: 2'-O-methylguanosine
<220> FEATURE:
<221> NAME/KEY: modified_base
<222> LOCATION: (17)..(17)
<223> OTHER INFORMATION: 2'-O-methyluridine
<220> FEATURE:
<221> NAME/KEY: modified_base
<222> LOCATION: (18)..(18)
<223> OTHER INFORMATION: 2'-O-methylguanosine
<220> FEATURE:
<221> NAME/KEY: modified_base
<222> LOCATION: (19)..(19)
<223> OTHER INFORMATION: 2'-O-methyladenosine
<220> FEATURE:
<221> NAME/KEY: modified_base
<222> LOCATION: (20)..(20)
<223> OTHER INFORMATION: 2'-O-methyluridine
<220> FEATURE:
<221> NAME/KEY: modified_base
<222> LOCATION: (21)..(21)
<223> OTHER INFORMATION: 2'-O-methylguanosine
<220> FEATURE:
<221> NAME/KEY: modified_base
<222> LOCATION: (22)..(22)
<223> OTHER INFORMATION: 2'-O-methyluridine
<220> FEATURE:
<221> NAME/KEY: modified_base
<222> LOCATION: (23)..(23)
<223> OTHER INFORMATION: 2'-O-methylcytidine
<220> FEATURE:
<221> NAME/KEY: modified_base
<222> LOCATION: (24)..(24)
<223> OTHER INFORMATION: 2'-O-methylguanosine
<220> FEATURE:
<221> NAME/KEY: modified_base
<222> LOCATION: (26)..(26)
<223> OTHER INFORMATION: 2'-O-methylguanosine
<220> FEATURE:
<221> NAME/KEY: modified_base
<222> LOCATION: (27)..(27)
<223> OTHER INFORMATION: 2'-O-methyladenosine
<220> FEATURE:
<221> NAME/KEY: modified_base
<222> LOCATION: (28)..(28)
<223> OTHER INFORMATION: 2'-O-methylcytidine

<400> SEQUENCE: 4
gucaccucag cguaagugau gucgtgac                                           28
```